(12) United States Patent
Moreland et al.

(10) Patent No.: US 12,036,007 B2
(45) Date of Patent: Jul. 16, 2024

(54) MONITORING APPARATUS AND METHOD

(71) Applicant: CURRENT HEALTH LIMITED, Edinburgh (GB)

(72) Inventors: Sam Moreland, Edinburgh (GB); Stewart Whiting, Edinburgh (GB)

(73) Assignee: CURRENT HEALTH LIMITED, Edinburgh (GB)

( * ) Notice: Subject to any disclaimer, the term of this patent is extended or adjusted under 35 U.S.C. 154(b) by 574 days.

(21) Appl. No.: 17/283,841

(22) PCT Filed: Oct. 8, 2019

(86) PCT No.: PCT/GB2019/052839
§ 371 (c)(1),
(2) Date: Apr. 8, 2021

(87) PCT Pub. No.: WO2020/074872
PCT Pub. Date: Apr. 16, 2020

(65) Prior Publication Data
US 2021/0378534 A1 Dec. 9, 2021

(30) Foreign Application Priority Data
Oct. 11, 2018 (EP) .................................... 18199988

(51) Int. Cl.
*A61B 5/024* (2006.01)
*A61B 5/00* (2006.01)
(Continued)

(52) U.S. Cl.
CPC ........ *A61B 5/02427* (2013.01); *A61B 5/0022* (2013.01); *A61B 5/02028* (2013.01);
(Continued)

(58) Field of Classification Search
None
See application file for complete search history.

(56) References Cited

U.S. PATENT DOCUMENTS

| 5,497,769 A | 3/1996 | Gratton |
| 9,526,431 B2 | 12/2016 | Zakharov et al. |

(Continued)

FOREIGN PATENT DOCUMENTS

| WO | WO 2015/101947 | * 7/2015 |
| WO | 2015/171667 | 11/2015 |

(Continued)

OTHER PUBLICATIONS

Communication under Rule 71(3) PCT dated Aug. 11, 2022 issued for European Application No. 18 199 988.9 (56 pages).
(Continued)

*Primary Examiner* — Katherine L Fernandez
(74) *Attorney, Agent, or Firm* — Nixon & Vanderhye P.C.

(57) ABSTRACT

Monitoring apparatus for monitoring the pulse transit time and/or estimating one or more blood pressure parameters of a subject and the method of use of the monitoring apparatus. The apparatus comprises an upper arm unit for attaching to a subject's upper arm in use and comprising at least one motion sensor, a photoplethysmograph comprising at least one light source and at least one light detector and at least one display.

15 Claims, 13 Drawing Sheets

(51) Int. Cl.
*A61B 5/02* (2006.01)
*A61B 5/021* (2006.01)

(52) U.S. Cl.
CPC ........ *A61B 5/02125* (2013.01); *A61B 5/6824* (2013.01); *A61B 5/7221* (2013.01); *A61B 5/7246* (2013.01); *A61B 2562/0219* (2013.01)

(56) References Cited

U.S. PATENT DOCUMENTS

| | | | |
|---|---|---|---|
| 11,759,121 B2* | 9/2023 | Mccann | A61B 5/0295 600/484 |
| 2008/0039731 A1* | 2/2008 | McCombie | A61B 5/02255 600/485 |
| 2008/0081961 A1 | 4/2008 | Westbrook et al. | |
| 2008/0303660 A1 | 12/2008 | Lombardi | |
| 2010/0297978 A1 | 11/2010 | McClenny et al. | |
| 2010/0298650 A1 | 11/2010 | Moon et al. | |
| 2011/0054277 A1 | 3/2011 | Pinter et al. | |
| 2011/0066007 A1 | 3/2011 | Banet et al. | |
| 2012/0154157 A1 | 6/2012 | George | |
| 2012/0203077 A1 | 8/2012 | He et al. | |
| 2013/0116520 A1 | 5/2013 | Roham et al. | |
| 2013/0324816 A1 | 12/2013 | Bechtel | |
| 2013/0331058 A1 | 12/2013 | Harvey | |
| 2013/0338460 A1 | 12/2013 | He et al. | |
| 2014/0228657 A1 | 8/2014 | Palley et al. | |
| 2014/0276175 A1 | 9/2014 | Banet et al. | |
| 2015/0305632 A1 | 10/2015 | Najarian et al. | |
| 2015/0313484 A1 | 11/2015 | Burg et al. | |
| 2016/0007934 A1 | 1/2016 | Arnold et al. | |
| 2016/0007935 A1 | 1/2016 | Hernandez et al. | |
| 2016/0022220 A1* | 1/2016 | Lee | A61B 5/02433 600/479 |
| 2016/0051205 A1 | 2/2016 | Al-Ali et al. | |
| 2016/0220122 A1 | 8/2016 | Luna et al. | |
| 2016/0302677 A1* | 10/2016 | He | A61B 5/1102 |
| 2017/0119314 A1 | 5/2017 | Just | |
| 2017/0251935 A1 | 9/2017 | Yuen | |
| 2019/0261890 A1 | 8/2019 | Li | |
| 2019/0282180 A1 | 9/2019 | Babaeizadeh | |
| 2019/0357850 A1 | 11/2019 | Li et al. | |

FOREIGN PATENT DOCUMENTS

| | | |
|---|---|---|
| WO | 2016/083807 | 6/2016 |
| WO | 2017/220526 | 12/2017 |

OTHER PUBLICATIONS

Eric S. Winokur et al., "A Wearable Vital Signs Monitor at the Ear for Continuous Heart Rate and Pulse Transit Time Measurements", 34th Annual International Conference of the IEEE EMBS, San Diego, California USA, Aug. 28-Sep. 1, 2012 (4 pages).
Third-Party Submission Under 37 CFR 1.290 issued in U.S. Appl. No. 16/633,077 (15 pages).
International Search Report and Written Opinion of the ISA for PCT/GB2019/052839 dated Dec. 11, 2019, 11 pages.
Walter Karlen, et al., "Multiparameter Respiratory Rate Estimation From the Photoplethysmogram", IEEE Transactions on Biomedical Engineering, vol. 60, No. 7, Jul. 2013, 9 pages.
International Search Report and Written Opinion of PCT/GB2018/053420 dated Mar. 20, 2019, 10 pages.
International Preliminary Report on Patentability of PCT/GB2018/053420 dated Nov. 18, 2019, 6 pages.
Third Party Observations and Submission of Prior Art in the examination proceedings of European Patent Application No. 17204223.6 (8 pages).

* cited by examiner

MONITORING APPARATUS AND METHOD

This application is the U.S. national phase of International Application No. PCT/GB2019/052839 filed Oct. 8, 2019 which designated the U.S. and claims priority to EP Patent Application No. 18199988.9 filed Oct. 11, 2018, the entire contents of each of which are hereby incorporated by reference.

FIELD OF THE INVENTION

The present invention relates to the field of wearable devices for monitoring physiological parameters of a subject.

BACKGROUND TO THE INVENTION

It is desirable to automatically measure the blood pressure (BP) of a subject to facilitate medical monitoring over a period of time. The measurement of BP is important because higher systolic pressure leads to left ventricular hypertrophy which is related to a range of medical issues (e.g. ischemia) and is one of the prime predictors of premature morbidity. If the symptom of high BP is found in a subject, steps can be taken to reduce the likelihood of such issues and/or to reduce their severity.

Blood pressure measuring devices are usually in the form of either non-invasive inflatable cuffs (sphygmomanometers), or invasive strain gauges in fluid contact with blood within an artery. However, such devices are cumbersome and uncomfortable and acquiring a measurement of BP with them can be time consuming. They are not suitable for use while the subject is moving around or sleeping, and they are used to measure BP instantaneously and hence are not suitable for continuous monitoring (e.g. over a period of several days). Repeated measurements with inflatable cuffs are not recommended because their use increases the workload of the heart and causes circulatory interference at the measurement site. Additionally, BP is known to fluctuate over short time periods (i.e. time periods comparable for the time required to carry out a measurement using a sphygmomanometer) due to respiratory effects, and thus it is likely that measurements are taken which do not accurately represent the mean BP of a subject, or indeed the subject's general health.

Pulse transit time (PTT) is the time for a pulse pressure wave to travel between two arterial sites, for example, between a first body part and a second body part. PTT has been shown to be covariant with systolic blood pressure (SBP). If arterial BP increases, arterial wall tension increases (i.e. arterial compliance decreases) and PTT decreases. As such, it would be useful to measure PTT (and the rate of change of PTT) and to thereby deduce BP (and the rate of change of BP). Additionally, as BP is known to vary considerably over short time periods, a reliable method of measuring PTT may be independently useful as a measurement of health because PTT is not affected by respiratory effects.

Pulse wave velocity (PWV) is the speed of a pressure pulse propagating along the arterial wall and can be calculated from PTT. The velocity of a longitudinal pressure wave (e.g. the PWV) is related to the elasticity of the arterial vessel and to the vessel dimension. PWV depends on both the arterial pressure and the intrinsic elastic properties of the arterial wall (PWV increases as BP increases).

Typically, PTT is measured using Electrocardiogram (ECG) proximal timing (i.e. timing the difference between depolarisation of the heart and the pulse arriving at a pulse oximeter mounted on a digit or at the ear). It is also known to determine BP from the pulse transit time using ballistocardiography (BCG). The BCG is a measurement of the reaction forces of the body to cardiac ejection of blood into the aorta and contraction of the ventricles, i.e. the vibrations produced in the body from the contraction of the heart muscles are measured.

It is known to carry out ballistocardiograph measurements at the sternum and, more recently, wearable BCG sensors have become available. However, these have not been combined with a measurement of PTT to continuously (e.g. for several hours) monitor parameters relating to changes in BP. The use of a finger-mounted pulse oximeter alongside a sternum-mounted BCG to measure PTT is the standard method, however this is cumbersome and not suitable if a subject wishes to move around and thus is also not suitable for use in continuous monitoring. The use of BCG without such a finger mounted device has historically been limited due to noise in the BCG signal.

A second method of measuring cardiac activity is Photoplethysmography (PPG). PPG is an optical technique that can be used to detect changes in the blood volume within a vessel. It can be used to non-invasively monitor a subject's pulse at the surface of the skin. FIG. 5 is a plot of a typical example of a PPG waveform in which the systolic activity (including the anacrotic limb due to the opening of the aortic valve) and the diastolic activity (including the dicrotic notch due to closure of the aortic valve) are both clearly visible. FIG. 6 is a plot of a typical example of a BCG waveform in which the same cardiac activity can be deciphered (for example, point 214 is the dicrotic notch). An analysis of the timing differences between the features (not limited to peaks and/or troughs) of the two waveforms can be used to calculate a PTT and optionally to thereby deduce the BP of a subject.

Accordingly, the invention seeks to provide a non-invasive, hygienic and ambulatory apparatus and a method for use of the apparatus, for monitoring parameters relating to BP, in particular for monitoring a PTT of a subject (for example the PTT between the subject's heart and the location of the apparatus, typically the upper arm) as well as changes in the PTT, and to thereby monitor the BP and changes in the BP of a subject.

SUMMARY OF THE INVENTION

According to a first aspect of the invention there is provided a monitoring apparatus for monitoring one or more pulse transit time (PTT) or blood pressure (BP) parameters, of a subject, or changes therein, the monitoring apparatus comprising an upper arm unit configured for attachment to a subject's upper arm, the upper arm unit comprising at least one motion sensor, the at least one motion sensor configured to monitor motion due to cardiac activity and output at least one motion signal while the upper arm unit is worn on the subject's upper arm, a photoplethysmograph (PPG) configured to monitor blood volume within the subject's upper arm and output a PPG signal while the upper arm unit is worn on the subject's upper arm, at least one processor programmed to process both the at least one motion signal and the PPG signal to thereby calculate an estimate of the one or more PTT or BP parameters of the subject, or changes therein.

Typically, the estimate of the one or more BP parameters of the subject is derived from the estimate of one or more PTT parameters of the subject. Both PTT and BP parameters can be useful physiological parameters in their own right. Monitoring changes in PTT parameters, even where there is some error in the measured values representative of the said PTT parameters can be useful as a method of monitoring the health of a subject, for example when compared to monitoring other parameters such as BP (e.g. systolic BP). Monitoring changes in PTT and BP parameters is of value even in the case that absolute values of such PTT or BP parameters are not found. Changes may be monitored in either absolute or relative values representative of the one or more PTT parameters and/or representative of the one or more BP parameters.

We have found that it is surprisingly advantageous to provide a monitor which comprises an upper arm unit comprising at least one motion sensor, the at least one motion sensor configured to monitor motion due to cardiac activity (for example, to thereby provide a BCG signal, the BCG signal comprising signal samples relating to a PTT between the heart and the upper arm), and a PPG, and to process the measurements from the at least one motion sensor and the PPG because:

- a sufficiently sensitive motion sensor in an upper arm unit can, in at least some body postures, directly detect motion due to cardiac activity, including motion related to a PTT between the heart and the upper arm;
- although the strength of the BCG signal is typically weaker at the upper arm position than at a subject's sternum, we have found that, surprisingly, the quality of the signal is still suitable for this kind of measurement and allows the subject to move around while the measurement is carried out;
- although the strength of the PPG signal is typically weaker at the upper arm position than at a subject's finger (where it would typically be measured), we have found that surprisingly, when a subject is moving, the quality of the signal is cleaner and more reliable than the signal measured at a finger;
- the upper-arm location means that the motion sensor has close proximity to ballistic displacement forces of blood from the heart into the aorta following ejection, without having to be in contact with the chest, but is sufficiently far enough from the heart to allow the PPG to measure PTTs of tens or hundreds of milliseconds, which is sufficient to enable accurate measurement.

Typically, the upper arm unit comprises a housing which includes the at least one motion sensor and the PPG therein. Typically, the upper arm unit comprises at least one motion sensor or preferably at least two motion sensors or more preferably at least three motion sensors. Typically, the at least one motion sensor comprises (e.g. is) a gyroscope (for example a microelectromechanical system (MEMS) gyroscope). Typically, the or each motion sensor will sense motion around one axis, typically orthogonal to the axis in which motion is sensed by one or each of the or each other motion sensors. Typically, the or each motion sensor will output at least one motion signal. For example, there may be three gyroscopes, each configured to measure rotational motion around one of the three Cartesian axes (for example, a first gyroscope would measure rotational motion around the x-axis and/or a second gyroscope would measure rotational motion around the y-axis and/or a third gyroscope would measure rotational motion around the z-axis) and output at least one motion signal (e.g. a motion signal corresponding to the measured motion). There may be three gyroscopes configured such that each gyroscope can measure one of pitch or roll or yaw.

A gyroscope does not need to be calibrated to take into account the effects of a gravitational field or local gravitational field changes (unlike, for example, an accelerometer).

In some embodiments the at least one motion sensor may comprise (e.g. be) an accelerometer. Optionally, the at least one motion sensor may comprise one or more accelerometers (e.g. three accelerometers), for example a multi-axis (e.g. two-axis or typically three-axis) accelerometer. An accelerometer measures movement because the upper arm can only move a limited distance and so movement leads to acceleration and deceleration within a short time period. Typically, where present, each accelerometer is configured to monitor motion in one of the three Cartesian directions (for example, a first accelerometer would measure motion across the x-axis and/or a second accelerometer would measure motion across the y-axis and/or a third accelerometer would measure motion across the z-axis) and output at least one motion signal (e.g. a motion signal corresponding to the measured motion).

It may be that the at least one motion sensor comprises one or more accelerometers and one or more gyroscopes. It may be that there are three accelerometers and three gyroscopes configured to provide measurements of motion in 6 axes.

Typically, the at least one processor comprises a clock, the clock configured to provide a shared clock signal for sampling of both the at least one motion signal and the PPG signal.

According to a second aspect of the invention there is provided a method of (e.g. continuously) monitoring one or more PTT or BP parameters (and/or continuously monitoring the one or more PTT or BP parameters) of a subject, or changes therein, using a monitoring apparatus, the monitoring apparatus comprising an upper arm unit, configured for attachment to a subject's upper arm (and typically attached to a subject's upper arm), the upper arm unit comprising at least one motion sensor the at least one motion sensor configured to monitor motion due to cardiac activity, (for example, a motion sensor configured to detect motion and to output at least one motion signal relating to pulse transit time between the heart and the upper arm) and output at least one motion signal while the upper arm unit is worn on the subject's upper arm, a PPG configured to monitor blood volume within the subject's upper arm and output a PPG signal while the upper arm unit is worn on the subject's upper arm, the method comprising processing both the at least one motion signal and the PPG signal to thereby calculate an estimate of the one or more PTT or BP parameters of the subject, or changes therein (optionally a rate of change of the one or more PTT or BP parameters of the subject), and then outputting the calculated estimate of the one or more PTT or BP parameters of the subject, or changes therein.

The method may further comprise processing both the at least one motion signal and the PPG signal to thereby calculate an estimate of the rate of change of the one or more PTT parameters of the subject, and then outputting the calculated estimate of the rate of change of the one or more PTT parameters of the subject. In some embodiments the method may comprise processing the estimate of the one or more PTT parameters of the subject to thereby calculate an estimate of one or more BP parameters of the subject and then outputting the calculated estimate of one or more BP parameters of the subject.

In some embodiments, the method may further comprise calculating a PPG and PTT based estimate of the BP (e.g. an estimate of systolic, diastolic, mean and/or arterial BP and/or one or more BP parameters). In some embodiments, the method may further comprise calculating a PPG and PTT based estimate of the rate of change of the one or more BP parameters. In some embodiments, the method may comprise calculating a correlation between the change in PTT and the BP (e.g. the changes in one or more PTT or BP parameters). The method may further comprise processing both the at least one motion signal and the PPG signal to thereby calculate an estimate of the rate of change of the one or more PTT parameters of the subject, and then outputting the calculated estimate of the rate of change of one or more PTT parameters of the subject.

In some embodiments the method may further comprise processing both the at least one motion signal and the PPG signal to thereby calculate an estimate of the rate of change of the one or more PTT parameters of the subject, and further processing the estimate of the rate of change of the one or more PTT parameters of the subject to calculate an estimate of the rate of change of the one or more BP parameters of the subject, and then outputting the calculated estimate of the rate of change of the one or more BP parameters of the subject, optionally wherein the processing comprises cross-calculating the at least one motion signal with the PPG signal. The method optionally may comprise calculating a correlation between the rate of change of one or more PTT parameters and the rate of change of one or more BP parameters.

The estimate of the one or more BP parameters may, for example, be an estimate of systolic blood pressure (SBP) and/or diastolic blood pressure (DBP) and/or mean blood pressure (MBP).

Typically, the said processing comprises cross-calculating the at least one motion signal with the PPG signal. For example, the method may comprise a step of cross-correlating (calculating a cross-correlation of) the motion signal with the PPG signal. The method may comprise calculating a cross spectral density of the motion signal with the PPG signal. Alternatively, or additionally, the method may comprise an autocorrelation step. The processing may comprise applying a plurality of signal processing techniques (e.g. filtering, (e.g. Fourier) transforming, comparing, cross-correlating, auto-correlating, inverting, modulating, demodulating, differentiating, etc.) to arrive at two waveforms with the same frequency and then comparing the two waveforms. Typically, the processing comprises comparing the phase of at least one waveform derived from a motion signal with the phase of at least one waveform derived from a PPG signal and optionally calculating a time difference between the two waveforms. Typically, the phase of a waveform derived from a motion signal and/or the phase of a waveform derived from a PPG signal may be a phase relative to an arbitrary reference point in a cardiac cycle. In some embodiments, the processing comprises calculating the difference in time between a first instant when a first feature appears in at least one waveform derived from a motion signal and a second instant when a corresponding feature appears in at least one waveform derived from a PPG signal.

Typically, the said processing comprises cross-correlating the at least one motion signal with the PPG signal and auto-correlating the PPG signal. However, in some embodiments it may be that the processing comprises cross-correlating the PPG signal with the at least one motion signal.

In some embodiments, the processing comprises (e.g. at least) cross-correlating the motion signal with the PPG signal and/or auto-correlating the PPG signal to thereby arrive at two waveforms, each of which comprises the same (e.g. integer) number of peaks per cardiac cycle and optionally comparing the phase of the two waveforms to thereby calculate an estimate of one or more PTT parameters. In some embodiments the processing may comprise using the (e.g. auto-correlated) PPG signal as a baseline signal and comparing the motion signal with this baseline signal throughout cardiac cycles signal to thereby calculate an estimate of the one or more PTT parameters. In some embodiments the processing may comprise extracting a waveform representative of a cardiac cycle from at least one motion signal by using the PPG signal as a reference and determining a timing difference between corresponding arbitrary points of the extracted waveform and a PPG derived waveform, optionally to thereby calculate an estimate of the one or more PTT parameters.

In some embodiments the one or more PTT parameters may comprise (e.g. be) an estimate of a PTT, for example an estimate of a PTT between the subject's heart and a location of the subject's upper arm.

This differs fundamentally from known techniques which detect peaks and/or troughs (e.g. local and/or global maxima and/or minima) in motion and/or PPG signals and measure the time between the two. The cross-calculation (e.g. cross-correlation or cross spectral density, and/or one or more phase differentiating functions) procedure processes a plurality (typically many) measurement data points per peak or trough of PPG signal. The cross-calculation procedure may be carried out, for example, on data sampled at at least 10 Hz, and typically more than 25 Hz, and potentially more than 50 Hz, or more than 100 Hz. Typically, data will be sampled at at least twice the frequency of the highest frequency of interest. Thus, the cross-calculation is not as affected by errors due to unpredictable and/or uncorrelated motion by a subject (e.g. motion due to the subject swinging their arm) and errors in determining the location of a maximum or minimum in a motion and/or PPG signal.

The motion signal may be determined from the output of more than one motion sensor, for example from the output of at least two or at least three gyroscopes and/or from the output of at least one accelerometer, for example by a process comprising summing the outputs from at least two or at least three gyroscopes and/or the output from at least one accelerometer. The PPG signal may be the output from the PPG without further data processing although typically preparing the PPG signal from the output of the PPG comprises at least filtering the output from the PPG. The motion and PPG signals are typically time series.

The processing may comprise cross-calculating (e.g. calculating a cross-correlation of or calculating a cross spectral density of) a plurality of different motion signals derived from the output of the at least one said motion sensor with a PPG signal derived from the output of the PPG. The outputs of the cross-calculation using different motion signals may be further processed (e.g. filtered, compared, averaged, summed, inverted, normalised, integrated, combined, etc.) to determine the calculated estimate of one or more PTT parameters and/or an estimate of the rate of change of the one or more PTT parameters (and in some embodiments to subsequently thereby determine an estimate of the one or more BP parameters and/or an estimate of the rate of change of the one or more BP parameters).

Cross-calculation (e.g. cross-correlation) comprises calculating the integral of the product of a first function with a second time-shifted function, across time shifts. Cross-correlation is therefore an asymmetric function. Preferably, the time-shifted function is the output of the PPG.

This is advantageous because the PPG signal measured at the upper arm is comparatively stable. The motion signal may be temporarily distorted by subject movements or high heart rates but by selecting the output of the PPG as the time-shifted function the measurements are more reliable than would be the case if the motion (e.g. gyroscope or accelerometer) data were selected. Furthermore, there are typically four peaks per cardiac cycle in a PPG signal versus one in a motion signal. We have found that the combination of upper arm-based motion sensing and PPG sensing with cross-calculation in which the output of the PPG is time shifted is surprisingly effective in providing good measurements of PTT (and/or measurements of the said one or more PTT parameters).

The said cross-calculating of the motion signal with the PPG signal may comprise processing a time window of the at least one motion signal (i.e. the at least one motion signal derived from the output of one or more motion sensors in a time window) and a time window (typically the same time window) of the PPG signal (i.e. the PPG signal derived from the output of the PPG during the time window, for example, wherein said windows of data were recorded concurrently) and performing a cross-calculation (e.g. cross-correlation or calculation of a cross spectral density) on the time window of the motion signal and the time window of the PPG signal.

The said processing may comprise calculating differentials of the at least one motion signal output by the one or more motion sensors. Thus, the motion signal may be determined from differentials between outputs of one or more motion sensor. The said processing may comprise applying one or more filters to the signals output by the one or more motion sensors.

The said processing may comprise analysing the delay between features of the motion sensor-derived BCG signal and features of the PPG signal. The said processing may comprise applying one or more filters (for example high pass filters, low pass filters, band pass filters, notch filters and/or any other filters or filtering methods, and/or combinations of filters) to filter noise from the motion sensor-derived BCG signal and/or the PPG signal. The said processing may comprise inverting the motion sensor-derived BCG signal and/or PPG signals. The said processing may comprise estimating one or more PTT parameters.

Typically, the PPG comprises at least one light source, the at least one light source comprising at least one LED and at least one light detector, the at least one light detector comprising at least one photodiode (e.g. on or under a light transmitting surface of the casing). Optionally the apparatus further comprises at least one display. The housing may have a light-transmitting incurvate subject-facing surface, (thereby increasing the contact area between the arm unit and the subject's arm). It may be that the radius of curvature of the light-transmitting, incurvate subject-facing surface is between 200 mm and 400 mm, or more preferably between 250 mm and 350 mm, or more preferably between 290 mm and 310 mm.

The apparatus may further comprise a display (or display output) configured to display (or output for display), an estimate of one or more PTT (and/or BP) parameters of the subject. Optionally the display may be configured to display (or output through the display output) a most recent estimate of one or more PTT (and/or BP) parameters and/or historic PTT (and/or historic BP) parameter estimates, for example in the form of a graph, or an average (e.g. mean) value for one or more PTT (and/or BP) parameters over a predetermined measurement period.

The apparatus may be configured to display the estimated one or more PTT (and/or BP) parameters on the display and/or may be configured to display a further parameter relating to the BP on the display. The estimated one or more PTT (and/or BP) parameters may comprise a most recent measurement of the one or more PTT (and/or BP) parameters and optionally information indicating variations in the one or more PTT (and/or BP) parameters. The further parameter relating to the BP may comprise a most recent measurement of the parameter and optionally information indicating variations in the parameter. The display may be part of the arm unit. The monitoring apparatus (e.g. the arm unit) may optionally further comprise a wireless transmitter configured to transmit data (e.g. the one or more estimated PTT (and/or BP) parameters) to at least one further device, for example a mobile device used by the subject or a medical professional, or to a remote server. The monitoring apparatus (e.g. the arm unit) may optionally further comprise a wireless transmitter configured to transmit (e.g. raw and/or partially processed) data (from the at least one motion sensor and PPG) to at least one further device, for example a remote server, where the one or more PTT (and/or BP) parameters is calculated (and optionally transmitted back to the apparatus or arm unit). In some embodiments the estimate of the one or more PTT parameters (and/or rate of change of PTT parameters and/or BP parameters and/or rate of change of BP parameters) may be (e.g. displayed) in the form of a number, optionally a number with arbitrary units, however it may be (e.g. displayed) in another form, for example as a phase in degrees or it may be represented in a non-numerical form.

The said processing may comprise analysing whether the output from the one or more motion sensors (e.g. the at least one motion signal) meets one or more quality criteria. The said processing may comprise analysing whether the combined output from the one or more motion sensors and/or the PPG results in a BCG signal and/or a PPG signal that meets one or more quality criteria (or optionally signals related to a BCG output that meets one or more quality criteria). The said processing may comprise analysing whether the output from the PPG (e.g. the PPG signal) meets one or more quality criteria.

Typically, the PPG signal will contain fewer noise features (e.g. features due to movement of the subject, for example movement due to the subject walking) than the at least one motion signal.

The said processing may comprise analysing whether the combined one or more motion signals results in a BCG output that meets one or more quality criteria. The said processing may comprise analysing whether the PPG signal meets one or more quality criteria.

The said processing may comprise calculating at least one (BCG- and PPG-derived) estimate of one or more PTT parameters (optionally an estimate of a PTT) by determining the delay between features relating to cardiac events (e.g. features caused by cardiac motion and/or cardiac activity) appearing in the motion and PPG signals. The said processing may comprise determining whether the said estimate of the one or more PTT parameters meets one or more accuracy criteria.

The said processing may comprise outputting (and the processor may output) a value of one or more PTT parameters calculated from the at least one estimate of the one or more PTT parameters, optionally only if the at least one estimate meets at least one quality criterion.

The said processing may comprise outputting (and the processor may output) an estimate of one or more BP parameters (e.g. systolic blood pressure (SBP)) calculated from the estimate of the one or more PTT parameters, optionally only if the estimate meets at least one quality criterion.

The said processing may comprise one or more signal processing steps, the signal processing steps comprising filtering, inverting, differentiating, cross-correlating and/or auto-correlating the at least one motion signal and/or the PPG signal.

The said processing may comprise outputting (and the processor may output) a continuous stream of data relating to one or more PTT parameters. The said processing may comprise outputting (and the processor may output) a continuous stream of data relating to one or more BP parameters, (e.g. SBP data), continuously calculated from the estimates of the one or more PTT parameters, optionally only if the estimate (or estimates) meets (or meet) at least one quality criterion. It may be that the stream of data relating to one or more PTT parameters and/or the stream of data relating to one or more BP parameters (e.g. SBP) is discrete data, for example the processor may output one measurement of one or more PTT and/or BP parameters per second, or per ten seconds, or one measurement of one or more PTT and/or BP parameters per minute. It may be that if the estimate of the one or more PTT parameters does not meet at least one quality criterion, the measurement resulting from that estimate is omitted from the stream of data relating to the one or more PTT parameters and/or is not used to calculate an estimate of one or more BP parameters.

In some embodiments the processor may be integrated in the upper arm unit, however, in other embodiments the processor, or one or more additional processors may be remote from the upper arm unit, for example the processor or one or more additional processors may be integrated in a mobile device of the subject or of a medical professional or may be integrated in a remote server.

Processing the one or more motion signals may comprise processing gyroscope-derived measurements of the rate of rotation around at least one, or at least two, or at least three (e.g. three) different (typically orthogonal) axes independently. Processing measurements of the rate of rotation around an axis may comprise carrying out frequency domain analysis of the measurements of rate of rotation to determine a peak in a frequency spectrum associated with the contraction of the heart, the one or more gyroscopes detecting the resulting vibrations when the vibrations reach the upper arm. Processing measurements of the rate of rotation around an axis may comprise detecting heart contraction induced variations in a property (e.g. amplitude or intensity) of the measurements of the rate of rotation. The heart contraction induced variations may be autocorrelated to determine a frequency peak, optionally within a predetermined boundary frequency range, for example by determining the most frequent correlation lag observation).

Alternatively or additionally, processing the one or more motion signals may comprise processing accelerometer-derived measurements of the acceleration along at least one, or at least two, or at least three (e.g. three) different (typically orthogonal) axes independently. Processing measurements of the acceleration along an axis may comprise carrying out frequency domain analysis of the measurements of acceleration to determine a peak in a frequency spectrum associated with contraction of the heart, the one or more accelerometers detecting the resulting vibrations when the vibrations reach the upper arm. Processing measurements of acceleration along an axis may comprise detecting heart contraction induced variations in a property (e.g. amplitude or intensity) of the measurements of the rate of motion. The heart contraction induced variations may be auto-correlated to determine a frequency peak, optionally within a predetermined boundary frequency range, for example by determining the most frequent correlation lag observation).

It may be that the processor is configured to process (and the method may comprise processing) both the at least one motion signal and the PPG signal to create concurrent data windows (e.g. a sub-section of the motion sensor data (a motion signal sample window) and a sub-section of the PPG data (a PPG signal sample window) that share the same time period). It may be that the processor is configured to process (and the method may comprise processing) a motion signal sample window and a PPG signal sample window to calculate a cross-calculation (e.g. a cross-correlation) of the motion signal sample window with the PPG signal sample window. It may be that the processor is configured to process (and the method may comprise processing) a said motion signal sample window and a said PPG signal sample window to detect features due to cardiac motion (e.g. motion due to a heartbeat) within the said motion signal sample window and/or within the said PPG signal sample window.

It may be that a signal sample window (e.g. a motion signal sample window and/or a PPG signal sample window) contains at least 10 data points, or preferably at least 100 data points, or more preferably at least 500 data points. It may be that a signal sample window (e.g. a motion signal sample window and/or a PPG signal sample window) consists of data recorded over at least 5 seconds, or preferably at least 10 seconds, or more preferably at least 30 seconds. It may be that a signal sample window (e.g. motion signal sample window and/or a PPG signal sample window) consists of data recorded over less than 180 seconds, or preferably less than 120 seconds, or preferably less than 60 seconds, or more preferably less than 45 seconds. In an alternative embodiment, the signal sample window may comprise (e.g. be) a long timescale signal sample window, wherein the long timescale signal sample window consists of data recorded over at least 30 minutes, or at least 1 hour, or at least 4 hours, or more preferably at least 8 hours. Typically, different (usually overlapping) motion signal sample windows and corresponding PPG signal sample windows are analysed periodically (for example, every 1-5 seconds) to provide revised estimates of, for example, one or more PTT and/or BP parameters. Typically (e.g. preferably), a signal sample window (e.g. a motion signal sample window and/or a PPG signal sample window) contains a plurality of samples for each cardiac cycle.

It may be that the motion signal and the PPG signal which are cross-calculated (e.g. cross-correlated or for which the cross-power density it calculated) each comprise at least 20, or at least 50 data points per cardiac cycle, and typically also extend across a plurality of cardiac cycles. Cross-calculating (e.g. cross-correlating or calculating the cross-power density of) at least 20 data points per cardiac cycle differs fundamentally from determining the position of individual points (e.g. maxima or minima, or maxima or minima of a first or a second differential) in the motion and PPG signals.

It may be that the processor is configured to process (and the method may comprise processing) the cross-calculation results (i.e. the resulting data from performing a cross-calculation (e.g. a cross-correlation) of a motion signal sample window with a PPG signal sample window) to detect features within the cross-calculation results that were caused by cardiac motion and/or cardiac activity. It may be that the processor is configured to process (and the method may comprise processing) the cross-calculation results to detect at least one feature in a motion signal sample window and at least one feature in a PPG signal sample window wherein the at least one feature in the motion signal sample window was caused by the same cardiac event as the at least one feature in the PPG signal sample window. It may be that the processor is configured to process (and the method may comprise processing) motion sensor data and/or PPG data to determine one or more time intervals between a plurality of features due to cardiac activity (e.g. cardiac motion). The plurality of features due to cardiac activity (e.g. cardiac motion) may comprise (e.g. be) features that are evident in one or more of the at least one motion signals, or features that are evident in the PPG signal, or both. The plurality of features due to cardiac activity (e.g. cardiac motion) may be evident in one or more of the at least one motion signals and/or evident in the PPG signal before any data processing. The plurality of features due to cardiac activity (e.g. cardiac motion) may be evident in one or more of the at least one motion sensor signals and/or evident in the PPG signal after some data processing (e.g. filtering), optionally only after some data processing.

The confidence status is typically selected from a plurality of confidence statuses. The confidence status may have a numerical value.

The output from the processing (carried out by the one or more processors) may for example be to a display, or to a memory, or to an input to another algorithm (which may be implemented by the same processor or a different one or more processors).

Typically, the plurality of confidence statuses includes at least one confidence status (indicative of a relatively low level of confidence) responsive to which no estimate of the one or more PTT parameters (and typically no estimate of the one or more BP parameters) is displayed (or output through the display output). The monitoring apparatus may not display (or output through the display output) an estimate of a current one or more PTT (or BP) parameters when the level of confidence in the estimate is too low (e.g. below a threshold or otherwise not meeting a confidence requirement).

A further at least two different confidence statuses indicative of different levels of confidence (e.g. a relatively high level of confidence and an intermediate level of confidence) may, in at least some circumstances, be displayed. It may be that both an estimate of the one or more PTT (and/or BP) parameters of the subject and data representative of the confidence status are displayed.

It may be that there is at least one confidence status (indicative of a relatively low level of confidence) responsive to which no estimate of the one or more PTT parameters (and typically no estimate of one or more BP parameters) is output (whether displayed, output to a display or output to any other processor). However, it may be that there is at least one confidence status (indicative of a relatively low level of confidence) responsive to which no estimate of the one or more PTT parameters (and typically no estimate of one or more BP parameters) is displayed (or output to a display output), but where an estimate of one or more PTT parameters (and/or an estimate of one or more BP parameters) is calculated and output for further processing. It may be that there is at least one confidence status responsive to which the previous estimate of one or more PTT parameters (and/or the previous estimate of one or more BP parameters) is output.

It may be that there is at least one confidence status responsive to which an average (e.g. mean), smoothed, weighted averaged and/or Kalman filtered estimate of the one or more PTT (and/or BP) parameters is output, wherein the estimate of the one or more PTT (and/or BP) parameters is calculated from at least 5, or at least 10, or at least 20 previous estimates of one or more PTT (and/or BP) parameters, or alternatively from at least the previous 10 minutes of data, of at least the previous 20 minutes of data, or of at least the previous 30 minutes of data. It may be that, when confidence in the calculated one or more PTT parameters (and/or calculated one or more BP parameters) does not meet a confidence requirement, it is preferable to not display an estimated PTT parameter (or an estimated BP parameter) at all, for example in case it was relied upon when it was not of sufficient accuracy. However, it may nevertheless still be useful to output the calculated estimate of one or more PTT parameters (and/or the calculated estimate one or more of BP parameters) for monitoring or further processing, for example for training of or processing by machine learning algorithms.

It may be that the plurality of confidence statuses includes at least two different confidence statuses indicative of different levels of confidence (e.g. a relatively high level of confidence and an intermediate level of confidence) wherein the respective confidence status the monitoring apparatus displays, or outputs through a display output, both an estimate of the one or more PTT parameters of the subject and data representative of the confidence status. It may be that the plurality of confidence statuses includes at least two different confidence statuses indicative of different levels of confidence (e.g. a relatively high level of confidence and an intermediate level of confidence) wherein the respective confidence status the monitoring apparatus displays, or outputs through a display output, both an estimate of one or more BP parameters of the subject and data representative of the confidence status. The data representative of the confidence status may be output as a numerical value or as a configuration of a graphical interface (e.g. colour, size, or position of a visual element). This enables a medical professional to assess the level of confidence in the estimate of the one or more PTT parameters (and/or the level of confidence in the estimate of the one or more BP parameters), while an estimate of the one or more PTT (and/or BP) parameters is displayed.

Therefore, it may be that when the level of confidence in the accuracy of the calculated estimate which fails to meet first confidence criteria (e.g. fails to exceed a threshold) an estimate of the one or more PTT (and typically of one or more BP) parameters is not displayed. It may be that when the level of confidence in the accuracy of the calculated estimate meets first confidence criteria but fails to meet second confidence criteria, the estimate of the one or more PTT (and/or BP) parameters is displayed but one or more signals indicative of limited confidence are also displayed. It may be that when the level of confidence in the accuracy of the calculated estimate meets third confidence criteria the estimate of the one or more PTT (and/or BP) parameters is displayed but either one or more signals indicative of a high level of confidence are displayed or one or more signals indicative of limited confidence are not displayed.

The at least one processor may be integral to the upper arm unit, but this is not required. The at least one processor may be part of one or more separate units, for example a mobile device used by the subject or a medical professional, or to a remote server, with which the upper arm unit is in electronic communication (for example through at least one wired or wireless interface) and the said determination may be distributed between at least one processor integral to the upper arm unit and at least one processor which is part of one or more separate units. The processing may take place within the upper arm unit, or remotely from the upper arm unit, or a combination thereof.

One or more (e.g. estimates of) PTT parameters may be expressed in any suitable units including units proportional to PTT, for example numerical estimates of one or more PTT parameters (e.g. in ms). Where calculated, the one or more BP parameters may be expressed in any suitable units including units proportional to the BP, for example numerical estimates of the one or more BP parameters (e.g. in mmHg).

DESCRIPTION OF THE DRAWINGS

An example embodiment of the present invention will now be illustrated with reference to the following Figures in which.

DETAILED DESCRIPTION OF AN EXAMPLE EMBODIMENT

Figure 1:
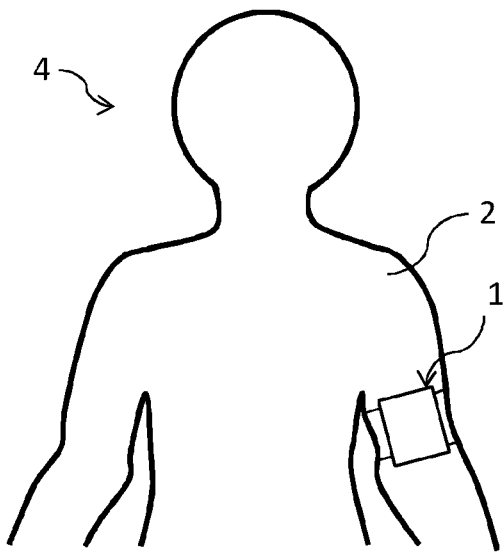
FIG. 1 is a diagram of a monitoring apparatus on the upper arm of a subject.
Figure 2:
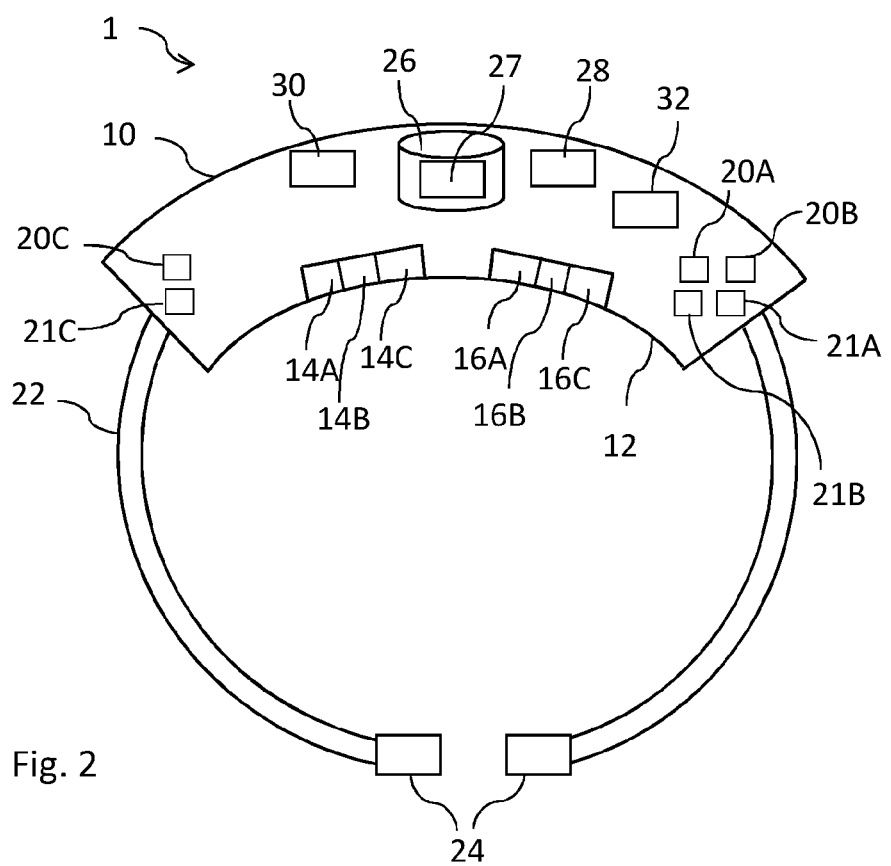
FIG. 2 is a cross-section through a monitoring apparatus.

With reference to FIGS. 1 and 2, the invention provides an ambulatory monitor (1), which is fitted to the upper arm (2) of a human subject (4) in use. The monitor is configured to measure a pulse transit time (PTT), in this example a PTT between a subject's heart and a location on a subject's arm) (which is an example of a PTT parameter) of the subject and typically also a number of physiological parameters (e.g. blood pressure (BP), pulse rate, etc.) of the subject, on a continuous basis.

The monitor (1) has a casing (10) with an incurvate subject-facing surface (12). Within the casing (10) there are three gyroscopes (20A, 20B, 20C) which measure rotation around three orthogonal axes, typically each gyroscope is formed by a three-axis solid state gyroscope device. The gyroscopes are fixed in position within the casing with a known orientation. They are calibrated during manufacture. An offset is determined for the gyroscopes so that measurements can be obtained of rotation around an axis in either sense. Further references to gyroscope measurement data refer to calibrated measurements, after allowing for the gyroscope offset.

The casing (10) also contains three accelerometers (21A, 21B, 21C) which measure acceleration along three orthogonal axes, typically each accelerometer is formed by a three-axis MEMS accelerometer device. The accelerometers are fixed in position within the casing with a known orientation and are calibrated during manufacture. Accelerometer data is processed to remove the signal caused by gravity. Further references to accelerometer measurement data refer to the calibrated measurements, after allowing for the subtraction of gravity from the accelerometer signals.

The casing also has a green light emitting diode (LED) light source (14A), a red LED light source (14B), an infra-red LED light source (14C) and first, second and third photosensors (16A, 16B, 16C). The light source and/or photosensors may be on the surface of the casing, underneath the surface of the casing (for example, covered by transparent windows) and/or within the body of the casing, in which case they may be connected to the surface of the casing through light guides. The light reflected from the LEDs and detected by the photosensors is captured as photoplethysmograph (PPG) data.

A strap (22) and clasp (24) hold the monitor in place on the upper arm (2) of the subject (4) during use. A microprocessor (26), in electronic communication with memory (28) controls the function of the monitor, including controlling the light source and processing measurements made by the gyroscopes and accelerometers (motion signals) and photosensor (PPG signals). The microprocessor further comprises a clock (27), configured to provide a common clock signal for sampling of both the motion signals and the PPG signals. There is also provided an input/output interface (30), including a screen and one or more buttons, and/or a touch screen, or a wired or wireless interface. The device has an integral power supply (32), formed by one or more batteries, and is ambulatory in that a subject (4) may walk around without removing the device or being connected to a monitoring device by a wire.

Motion due to the subject's (4) pulse is the result of the subject's heartbeat. This motion can be detected by the PPG as a change in blood volume and will be evident in features within the output PPG signal. The same heartbeat causes vibrations to travel along the subject's arterial walls. These vibrations will be detected by the gyroscopes and accelerometers and will be evident in features within the motion signals. Hence, an individual instance of the heart beating will result in features that can be found in both gyroscope and accelerometer-derived BCG data and in PPG data. However, due to other motions of the subject, the gyroscope and accelerometer-derived BCG data is likely to be noisy. Additionally, the speed of the vibrations that travel along the subject's arterial walls (as detected by the gyroscopes and accelerometers) are not the same as the speed of blood flow resulting in the subject's pulse (as detected by the PPG), there will therefore be some temporal delay between the corresponding features associated with each part of each cardiac cycle, in terms of when they appear in the two signals. This delay is indicative of the blood pressure (BP) (e.g. indicative of BP parameters, optionally indicative of systolic and/or diastolic and/or mean BP) of the subject.

During operation of the monitor, a ballistocardiograph (BOG) measurement signal is determined from the output of the gyroscopes and accelerometers (the motion signals). The gyroscopes and accelerometers detect motion of the subject (4), including motion due to cardiac activity (such as the heartbeat) of the subject. Specifically, the gyroscopes (20A, 20B, 20C) provide measurements of rotation around three orthogonal axes (e.g. an x-axis, a y-axis and a z-axis) and the accelerometers (21A, 21B, 21C) provide measurements of acceleration along three orthogonal axes. Most of the motion of the subject (e.g. motion due to the subject walking or due to twitching of the muscles) is filtered from the motion signals. This is achieved using standard digital filtering methods (as described below). Frequencies below 0.5 Hz and above 12 Hz are filtered from the signals (these frequencies are unlikely to be due to cardiac activity, for example, 0.5-4 Hz corresponds to 30-240 bpm, additionally these frequencies are unlikely to contain data relevant to a PTT or to the BP). Frequencies recorded in the motion signals that are due to cardiac activity (including the subject's pulse and the vibrations produced in the subject's body from the contraction of their heart muscles) are not filtered from the motion signals and the remaining, filtered motion signals are combined to make up the gyroscope and accelerometer-derived BCG data.

A PPG measurement signal is determined from the shallow pulse-rate measurement signal (indicative of reflected green light) and/or a deeper pulse-rate measurement signal (indicative of reflected red or IR light). The resulting PPG data is also filtered to remove signals due to non-cardiac motion of the subject (4), leaving behind signals due to cardiac motion such as the subject's pulse.

The PPG measurement signal utilises one or more of the green, red and IR wavelengths, dependent on the pulse-strength of the subject. The PPG measurement signal is indicative of the blood volume in the subject's (4) tissue adjacent to the monitor, in their upper arm, and hence is indicative of the subject's pulse at their upper arm. A higher blood volume leads to less reflected light, and vice versa.

The green light used for the measurement signal has a wavelength of 530 nm. The red light used for a reference signal has a wavelength of 660 nm. The IR light used for a reference signal has a wavelength of 950 nm.

Figure 3:
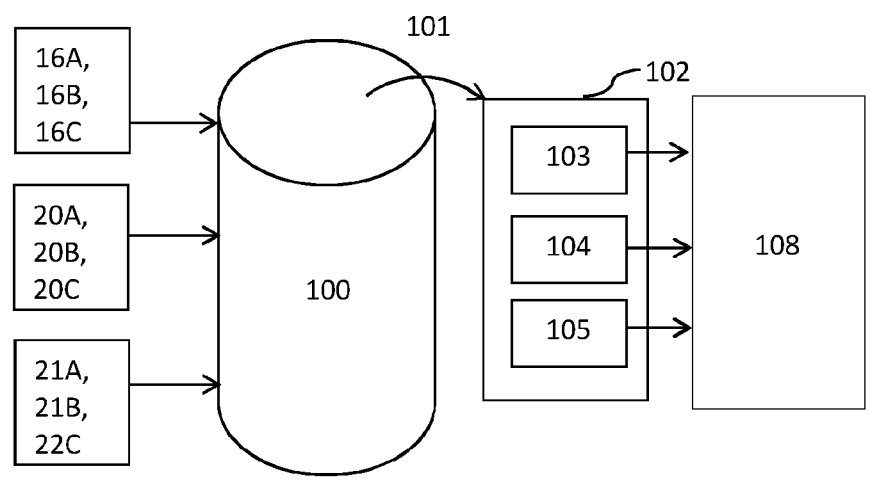
FIG. 3 is a flow chart of a general operating method.

A general operating procedure of the monitor is shown in overview in FIG. 3. Measurements are recorded from the first, second and third photosensors (16A, 16B, 16C), first, second and third gyroscopes (20A, 20B, 20C) and first, second and third accelerometers (21A, 21B, 21C). The measurements are made periodically and frequently, e.g. at 500 Hz, and the resulting gyroscope motion data, accelerometer motion data and PPG measurement data are stored as a time series in a data structure (100) in a solid-state memory for subsequent processing. The gyroscope motion sensor and the accelerometer motion data can then be processed to thereby provide BCG data.

Periodically, the stored gyroscope data, stored accelerometer data and the stored PPG data for a window of time are extracted (101) from the database by the processor and processed to determine an estimate of a PTT and/or of the BP (optionally an estimate of one or more PTT and/or BP parameters). The resulting data (102) for a specific window comprises a time series of motion signal data (103) (a combination of the rotation around each of the three axes and the acceleration along three axes), a resulting gyroscope and accelerometer-derived BCG signal (104) and a PPG signal (105). One skilled in the art will appreciate that the units in which these values are expressed is a matter of design choice. In an example, each window relates to 8 seconds of data samples at a sampling frequency of 500 Hz, i.e. 4,000 samples per sensor. The concurrency of corresponding data windows (e.g. a window of gyroscope and accelerometer-derived BCG data and a corresponding window of PPG data) is ensured by the use of a common clock signal. The said windows of data are then processed (108) as described below (and with reference to FIGS. 4A and 4B) in order to calculate and output an estimate of a PTT and/or the BP (e.g. an estimate of diastolic, systolic and/or mean BP) of the subject as well as a confidence level for the estimate of a PTT and/or the BP (e.g. an estimate of diastolic, systolic and/or mean BP). Extracting data may include copying it to a different location in memory, or simply identifying start and/or end points where it is stored.

The gyroscope and accelerometer-derived BCG signals and the PPG signal are then analysed to determine whether or not a clear signal has been obtained. If distinct cardiac cycles cannot be identified, or there are unacceptable gaps (e.g. greater than 10 s in duration) between identified cardiac cycles, these are indicative that the PPG data is not suitable and cannot be reliably used to generate PTT data, so the procedure stops. In some embodiments (as discussed below), an estimated BP (e.g. an estimated SBP) may still be output if a reliable estimate of PTT can be determined reliably from a combination of BCG data and previous PPG data and a reliable estimate of BP (e.g. SBP) can thereby be calculated.

In some cases, for example when the subject is in a high movement state, a given window of data will contain noisy (e.g. arrhythmic) data. As this could lead to an unreliable estimate of PTT and/or of BP (e.g. SBP, DPB, etc), windows of data containing more than a predetermined threshold level of noise are rejected and not used in PTT estimate calculations (and typically therefore are not used in any corresponding BP estimate calculations). However, such windows of data are still stored for optional subsequent processing, e.g. via a machine learning algorithm.

During operation the processor carries out processing steps through the use of an algorithm. One example embodiment of the algorithm has inputs including at least:
- a value sum of a set of samples of the x, y and z gyroscope and accelerometer waveforms (i.e. the x, y and z motion signals);
- an absolute differential value sum of the set of samples of the x, y and z gyroscope and accelerometer waveforms (i.e. the x, y and z motion signals);
- an absolute value of the samples of the y gyroscope waveform; and an absolute differential of the samples of the y gyroscope waveform.

In some embodiments the algorithm may alternatively or additionally have further inputs, such as an absolute value of the samples of the z gyroscope waveform or an absolute value of the samples of the y accelerometer waveform, or an absolute value of a combination of accelerometer and gyroscope waveforms, or some other motion signal input.

Each of these is first calculated by the processor, and then passed to a number of algorithms. The first algorithm applies a filter, for example a wide-band filter (e.g. a zero-phase $4^{th}$ order bandpass Butterworth filter) to remove frequencies outside the range of 0.5 Hz to 12 Hz from the said inputs to produce wide-band filtered waveforms. In some examples, the first algorithm may apply further alternative or additional filter to remove frequencies outside the range of 0.5 Hz to 4 Hz from the wide-band filtered waveforms to produce narrow-band filtered waveforms). The output of the first algorithm is a gyroscope and accelerometer-derived BCG signal. The narrow-band filtering steps have the result that the waveforms contain one BCG pulse per corresponding PPG pulse.

Figure 4A:
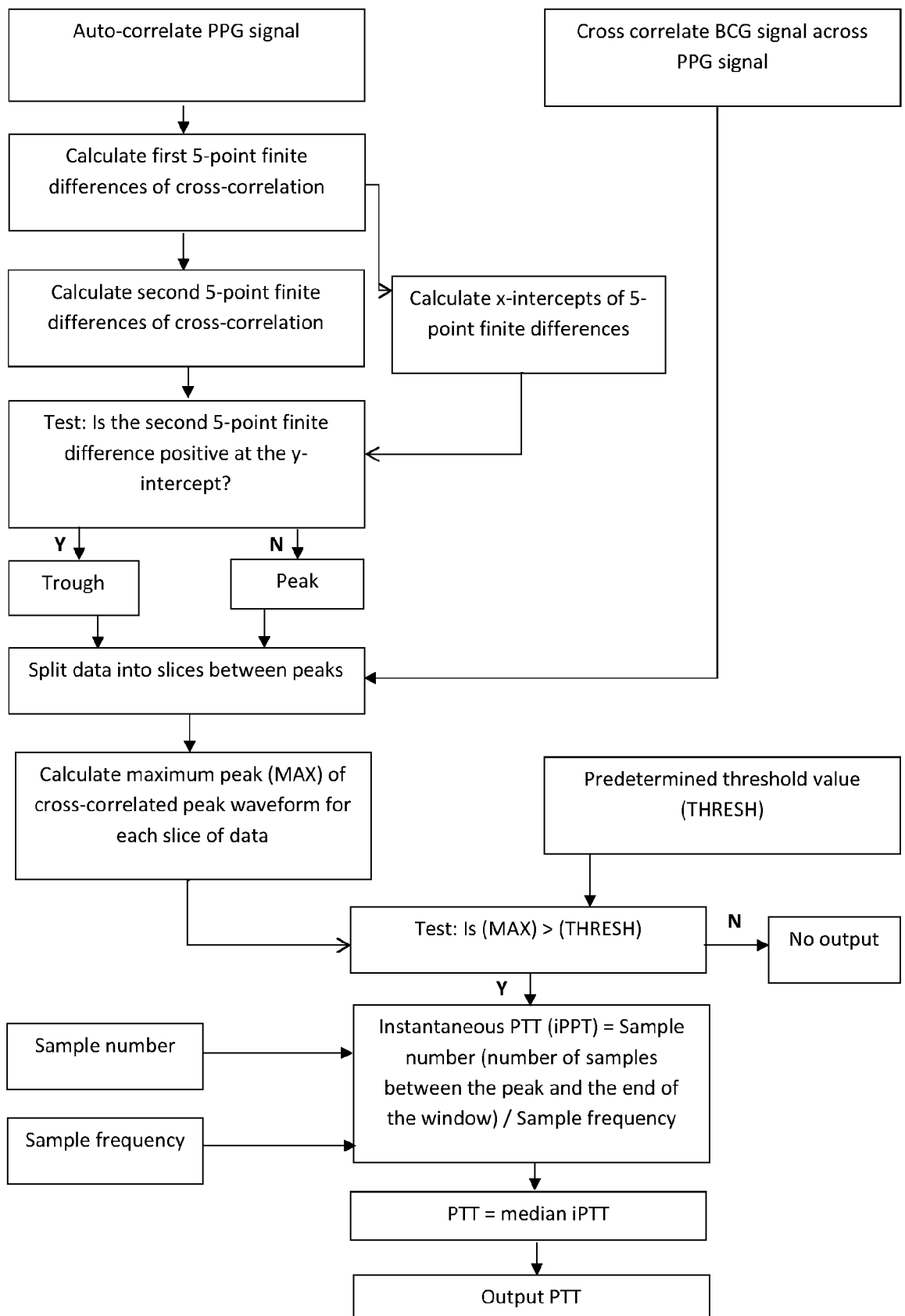
FIG. 4A is flow chart of a first example process for calculating a pulse transit time (PTT) parameter (e.g. a PTT) and photoplethysmograph (PPG) derived estimate of a BP parameter (e.g. a BP, optionally a systolic, diastolic, mean, etc, BP)

In a first example, detailed in FIG. 4A, each window of gyroscope-derived BCG data is cross-correlated with the corresponding concurrent window of PPG data. The cross-correlation provides a measure of similarity of the two windows of data. Features in the two windows of data that are due to the same cardiac event can thereby be identified, in spite of the fact that the features will appear in the gyroscope-derived BCG data and the PPG data at different times.

A second algorithm is used to apply a cross-correlation based approach. Because the PPG signal typically contains less noise and is more stable than the gyroscope and/or accelerometer-derived BCG signal, the PPG signal is used for the basis of cross-correlation in this approach. The cross-correlation based approach of the second algorithm includes the following steps:

- a cross-correlation of the gyroscope and accelerometer-derived BCG signal across the PPG signal to output a cross-correlation waveform;
- an autocorrelation of the PPG signal to output an autocorrelation waveform;
- a calculation of the 5-point finite differences of the cross-correlation to output a first 5-point difference waveform;
- a calculation of the 5-point different waveform to output a second 5-point difference waveform;
- a calculation the moments when the first 5-point difference waveform intercepts the 0-axis (i.e. when the function goes from having a positive value to a negative value or goes from having a negative value to a positive value) to output zero-moments;
- A peak-detection step to detect for each 0-moment whether the corresponding second 5-point difference waveform is positive or negative (a positive value for the second 5-point difference waveform indicates a trough and a negative value for the second 5-point difference waveform indicates a peak);
- A data-slicing step to divide both the cross-correlation waveform data and the autocorrelation waveform data into slices between each detected peak of the autocorrelation waveform;
- A maxima-detection step to find the maximum peak value of the cross-correlation waveform for each data slice;
- An instantaneous PTT (iPTT) calculation step in which the maximum peak value of the cross-correlation waveform for each data slice is compared to a predetermined threshold and in which, if the maximum value of the autocorrelation waveform is greater than the predetermined threshold, the iPTT is defined as the number of samples from the maximum cross-correlation peak to the end of the window, divided by the sample frequency;
- A PTT calculation step in which the PTT is calculated as the median of the iPTTs; and
- An output of a PTT.

In this example, the steps of the second algorithm are carried out in the order detailed above, however in other examples they may be carried out in other orders and in some examples two or more steps may be carried out simultaneously. Carrying out the cross-correlation approach of the second algorithm allows corresponding features to be accurately identified in the two data types.

The output PTT may then be used to calculate an estimate of pulse wave velocity (PWV) according to the following equation:

$$PWV = \frac{d}{PTT}$$

Wherein d is the distance that the vibrations due to cardiac activity have travelled. Typically, in this example, this is the arterial distance from the subject's (4) heart to the subject's upper arm (2). In examples where the monitor (1) is placed elsewhere, clearly d will be different.

PWV and PTT are affected by BP (e.g. systolic and/or diastolic and/or mean BP) and by arterial compliance. For example, an estimate of, the PWV can be calculated according to the following equation:

$$PWV = \sqrt{\frac{hE}{2r_0\rho}}$$

Wherein h is the thickness of the arterial wall, E is the Young's Modulus of the arterial wall, $r_0$ is the radius of the artery and $\rho$ is the density of the blood. In turn, the Young's Modulus of the arterial wall is pressure-dependent, such that, $$E = E_0 e^{\alpha P}$$

Wherein $E_0$ is the Young's Modulus of the arterial wall at zero pressure, $\alpha$ is a constant related to intrinsic elastic properties of the blood vessel and P is the (e.g. diastolic, systolic and/or mean) BP. Therefore, if an estimate of the PTT is calculated from the gyroscope and accelerometer-derived BCG and the PPG data, an estimate of the (e.g. diastolic, systolic and/or mean) BP of the subject can be found according to the following equation:

$$\text{Blood pressure} = \frac{1}{\alpha}\ln\frac{2r_0\rho(PWV)^2}{hE_0}$$

Unless the monitor (1) moves significantly, the distance (d) between the subject's (4) heart and the monitoring position at the subject's upper arm (2) is likely to remain constant. Similarly, over the course of a measurement, the Young's modulus of the arterial walls at zero pressure ($E_0$) is likely to remain constant. The changes in blood density (ρ), vessel radius ($r_0$) and arterial wall thickness are likewise unlikely to change significantly during, for example, a 30 second time interval. Therefore, these variables can be approximated to constants ($k_1$ and $k_2$), and hence a simplified equation can be provided to give an estimate of the BP of the subject (e.g. an estimate of diastolic, systolic and/or mean BP), based on the estimated PTT, as calculated from the gyroscope and accelerometer-derived BCG and the PPG:

$$\text{Blood pressure} = k_2 - k_1 \ln \text{PTT}^2$$

In some embodiments of the invention, the above equation may be used by the processor to calculate an estimate of the (e.g. diastolic, systolic and/or mean) BP of the subject (4). The estimate of the BP of the subject and/or of one or more BP parameters is then output.

Figure 4B:
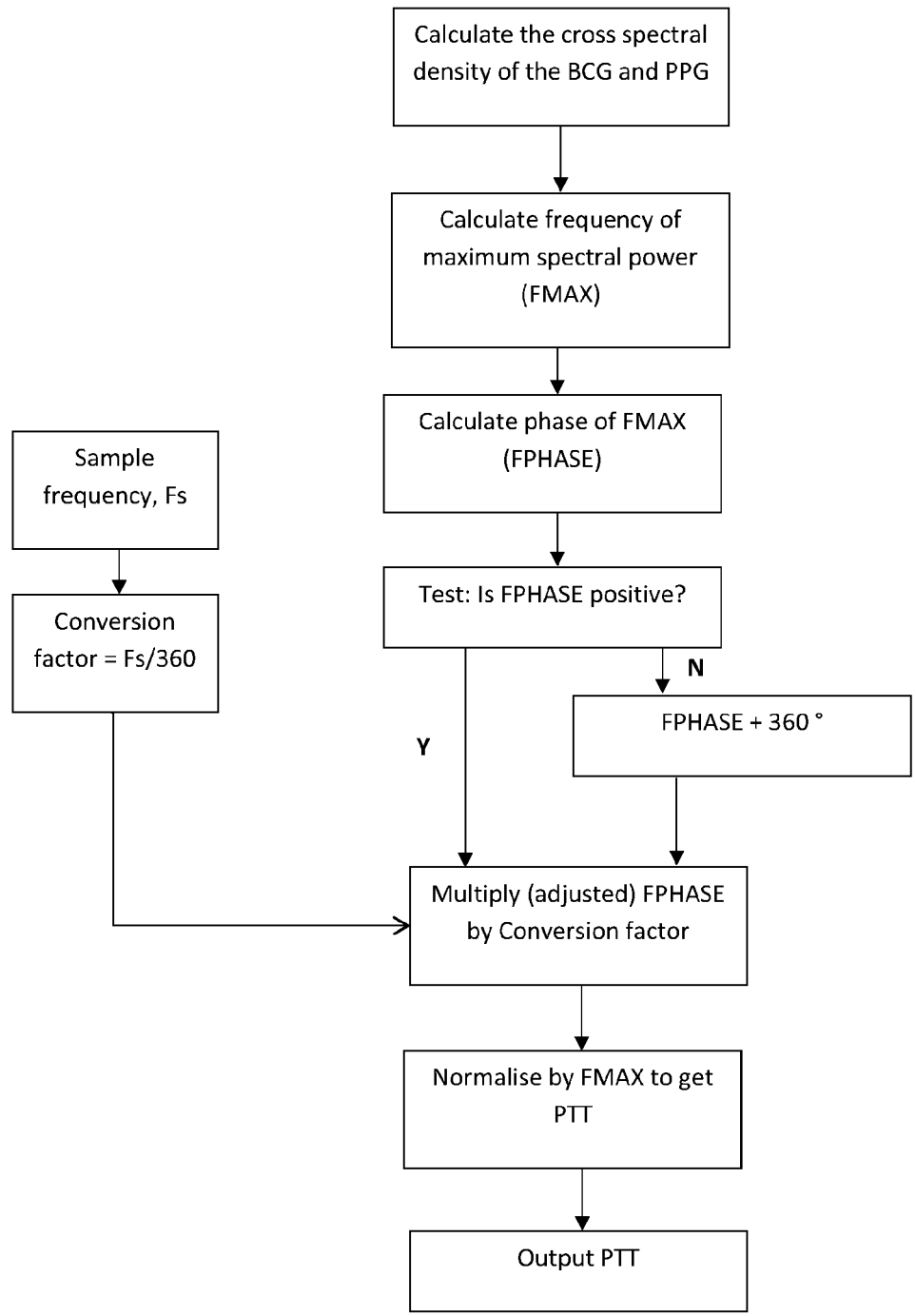
FIG. 4B is a flow chart of a second example process for calculating a PTT parameter (e.g. a PTT) and PPG derived estimate of a BP parameter (e.g. a BP, optionally a systolic, diastolic, mean, etc, BP)

In a second example, detailed in FIG. 4B, a third algorithm, different to the second algorithm is used instead of the second algorithm. The third algorithm is used to apply a cross spectral density approach. The cross spectral density approach includes the following steps:

A calculation of the cross spectral density of the PPG and BCG signals;
A calculation of the maximum spectral power;
A phase adjustment step in which the phase of the signal at the point in the signal that corresponds to the maximum spectral power is calculated and if it is negative it is converted by adding 360 degrees, resulting in a phase-adjusted signal;
A conversion factor step in which a conversion factor is calculated as the sampling frequency divided by 360;
A multiplication step in which the phase-adjusted signal is multiplied by the conversion factor, resulting in a pre-normalisation signal;
A PTT calculation step in which a PTT is calculated by normalising the pre-normalisation signal using the value of maximum spectral power; and
An output of the said PTT.

The output PTT may then be used to calculate the BP (e.g. the SBP) of the subject, as described in the first example and the BP of the subject is output.

In this example, the steps of the second algorithm are carried out in the order detailed above, however in other examples they may be carried out in a different order. In some examples two or more steps may be carried out simultaneously. Carrying out the cross-correlation approach of the second algorithm allows corresponding features to be accurately identified in the two data types.

Further, in some examples, multiple algorithms are used to find two or more estimates of a PTT. The two or more estimates of the said PTT are compared and, optionally, a value of PTT (either from the first estimate, or from the second or further estimates, of from an average (e.g. mean) of the estimates) is output only if the estimates each provide values of the said PTT that are within a predetermined range of each other.

Figure 9A:
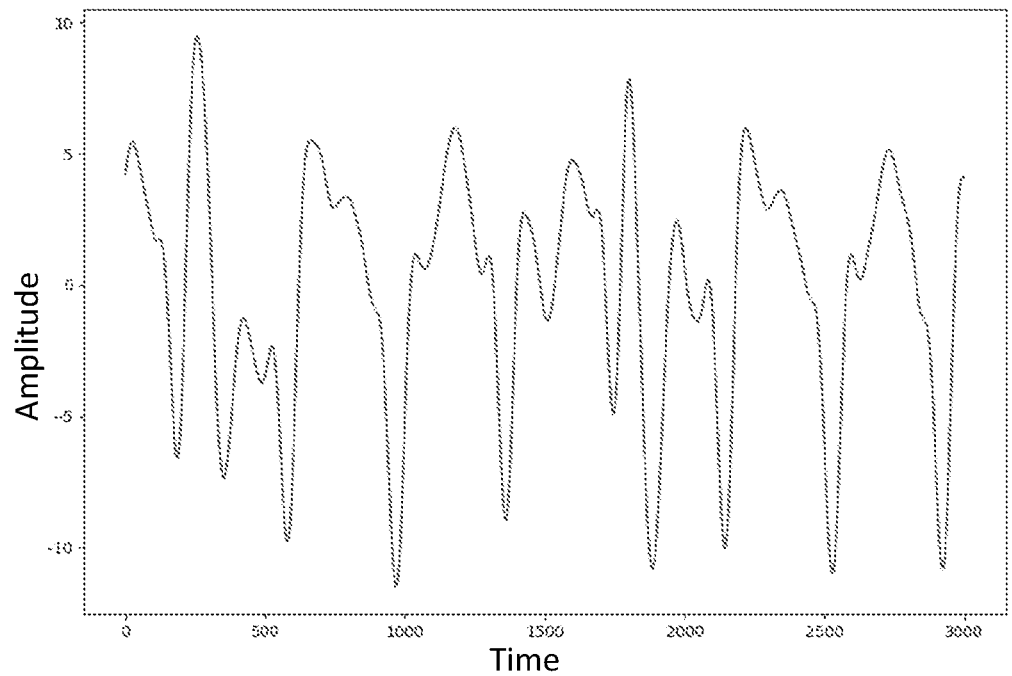
FIG. 9a is an example of filtered y-axis gyroscopic data and FIG. 9b is an example of the absolute differential of filtered y-axis gyroscopic data.

The motion signals for the measurement window are processed independently (i.e. the motion signal from each gyroscope and accelerometer (i.e. each axis) is processed independently). FIG. 9a shows example gyroscope data for the y-axis after filtering. The axes in which signals can be most clearly identified depend on the posture and/or movement pattern of the subject at the time in question.

Figure 5:
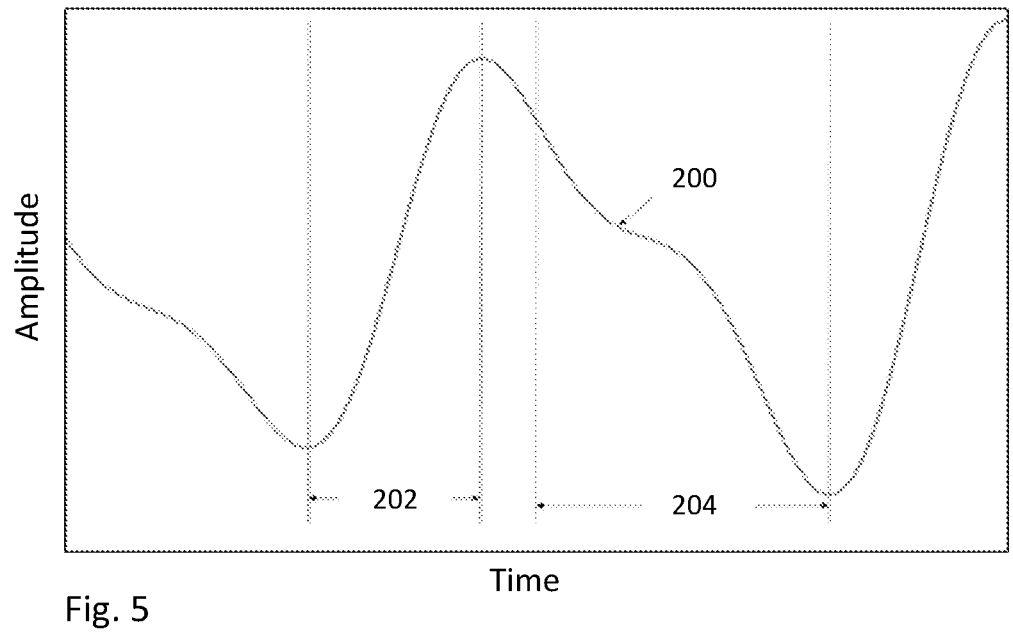
FIG. 5 is an example (PPG) waveform.
Figure 6:
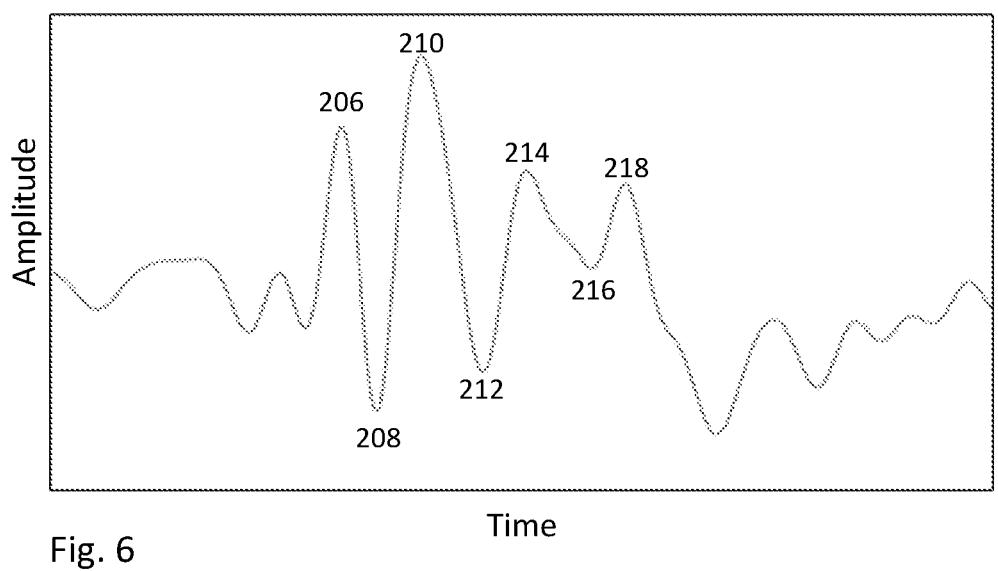
FIG. 6 is an example ballistocardiograph (BCG) waveform.

FIGS. 5-10 are plots of example signals, recorded either by the PPG or the gyroscopes, including processed data. FIG. 5 is an example of a PPG data set (i.e. a PPG signal sample window) associated with a cardiac cycle. Features in this data set include an anacrotic limb (202), a dicrotic notch (200) and a reverse wave. FIG. 6 is an example of a BCG data set (i.e. a gyroscope-derived BCG signal sample window) of the same cardiac cycle, including the rising moments of the anacrotic limb (initial rise of the anacrotic limb (206), maximal slew of the anacrotic limb (208) and crest of the anacrotic limb (210)), the crest of the systolic waveform (212), the dicrotic notch (214) and the reflective waveform (216, 218).

Figure 7:
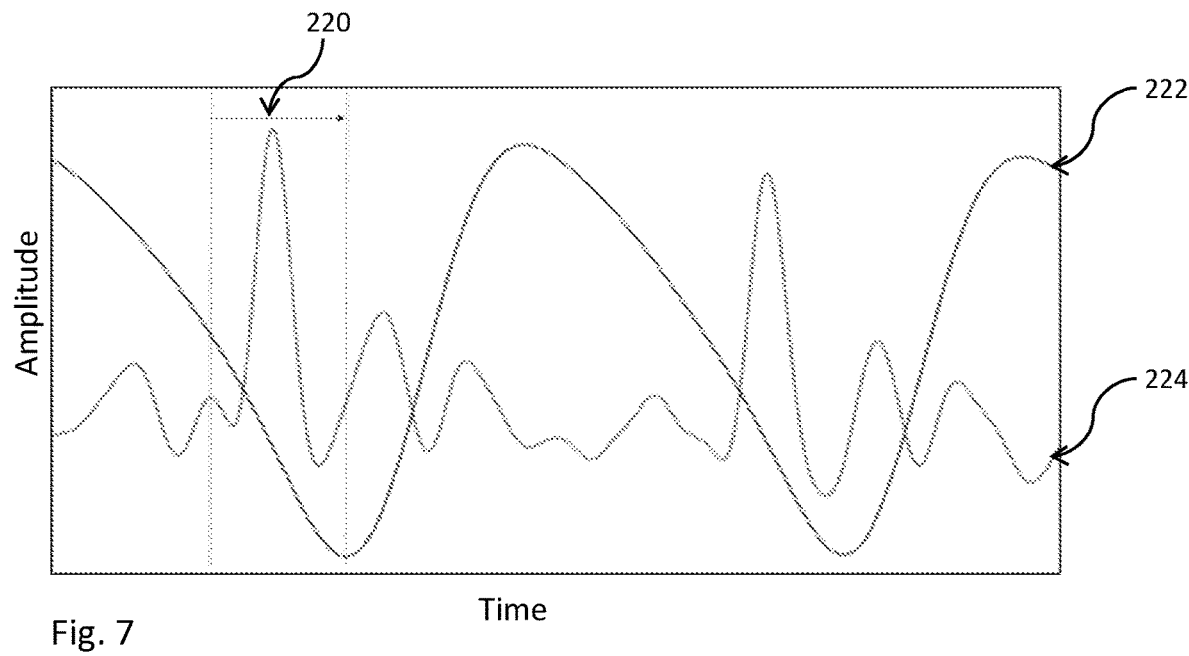
FIG. 7 is an example of concurrently measured motion sensor waveforms (including a BCG waveform) and PPG waveforms, recorded by a device positioned on the upper arm of a subject.

FIG. 7 is a plot of the example PPG data set (222) of FIG. 5 and the example BCG data set (224) of FIG. 6, displayed on the same axes. Here the delay (220) between features of the two data sets that both relate to the same event in the cardiac cycle can be seen.

Figure 8A:
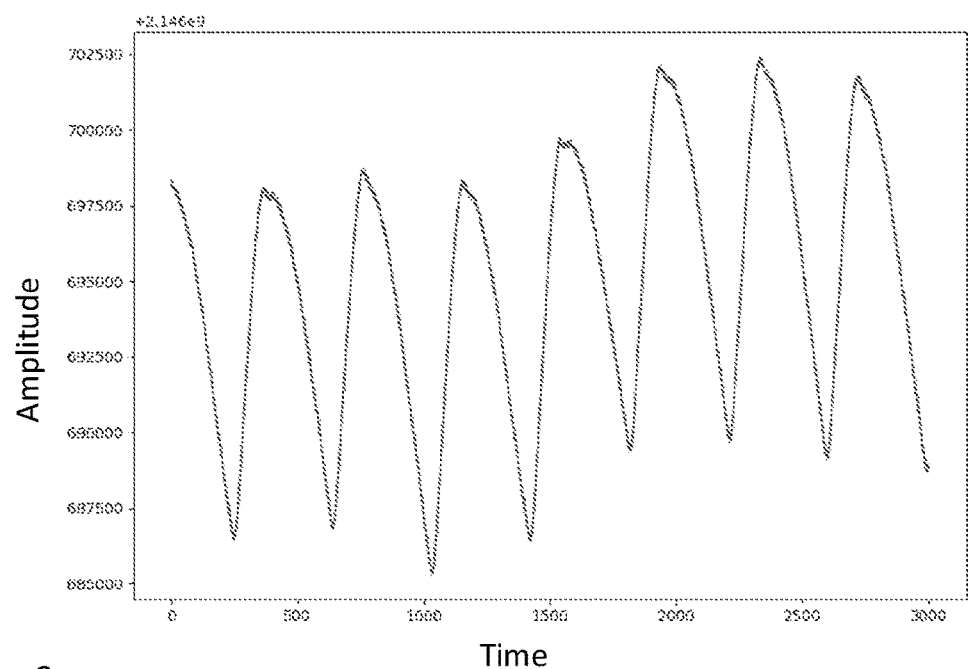
FIG. 8a is an example of a raw inverted PPG signal and FIG. 8b is the same data after filtering.
Figure 8B:
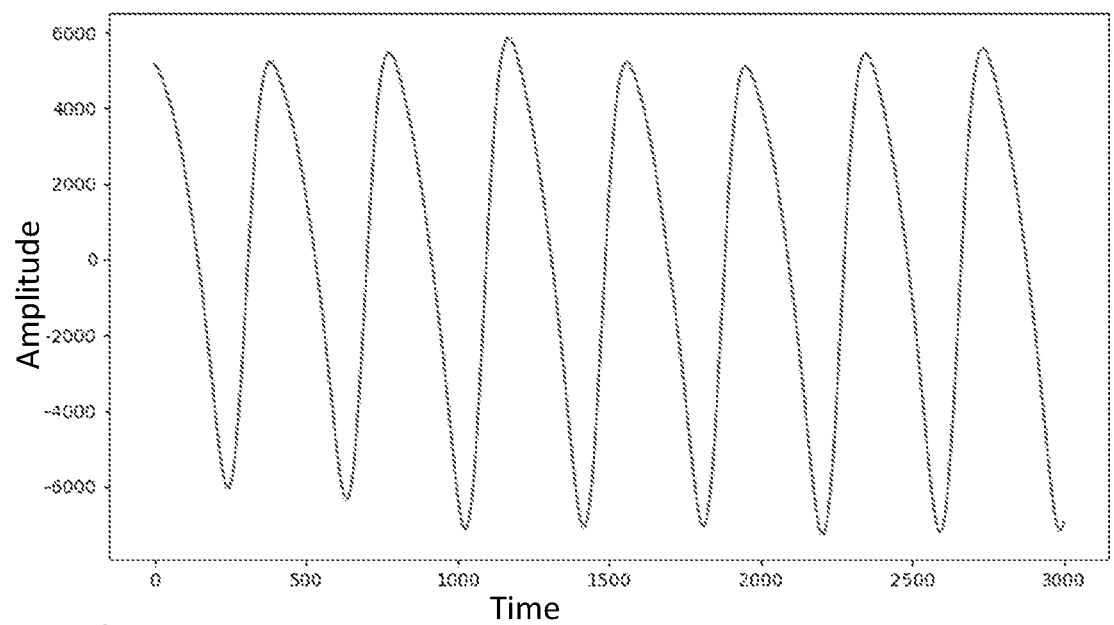

FIG. 8a is a plot of an example of PPG data (i.e. a PPG signal sample window). This data has been inverted. Noise within the data is visible, especially at the peaks of the waveform. FIG. 8b is the same PPG data, after the application of a $4^{th}$ Order (0.5-4 Hz) Butterworth bandpass zero-phase filter. This filter is applied to remove the noise that is visible in FIG. 8a.

Figure 9B:
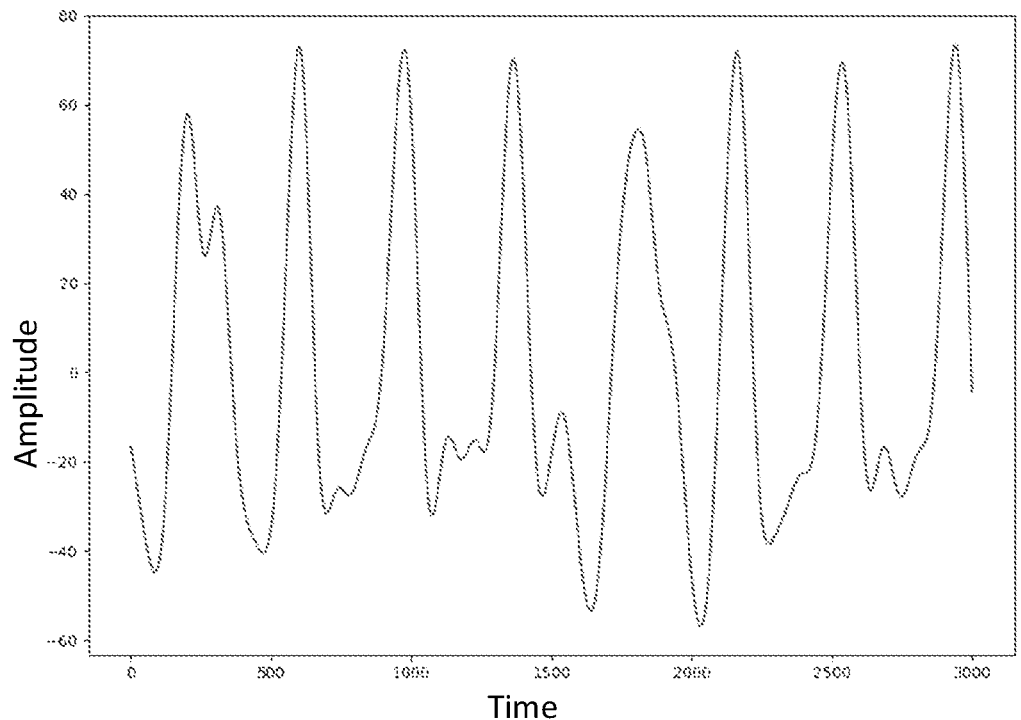
Figure 10:
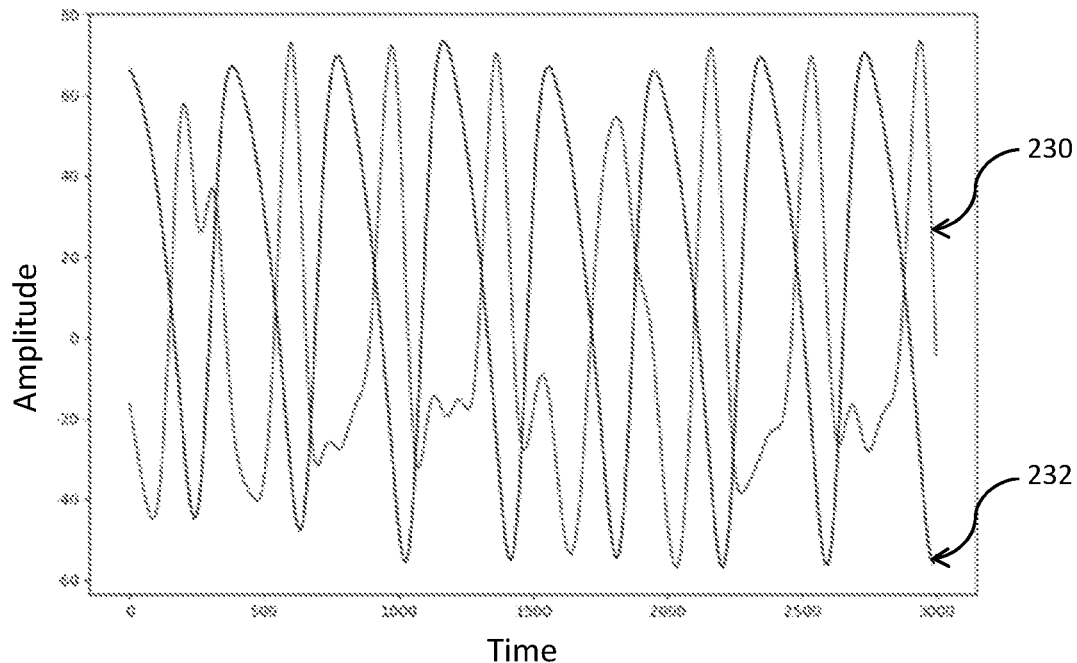
FIG. 10 is an example of the absolute differential of y-axis gyroscopic data after filtered and filtered PPG data.

For each limb of the PPG pulse wave, there are two waves for the BCG signal. Typically, the gyroscope and accelerometer-derived BCG signal is therefore at least four times the frequency of the PPG signal. FIG. 9a is a plot of filtered motion sensor signal data from a gyroscope measuring rotational motion around the y-axis and FIG. 9b is a plot of the filtered absolute differential of motion sensor signal data from a gyroscope measuring rotational motion around the y-axis. FIG. 10 is a plot of both the filtered absolute differential of motion sensor signal data from a gyroscope measuring rotational motion around the y-axis (230) and corresponding filtered PPG data (232).

Figure 11:
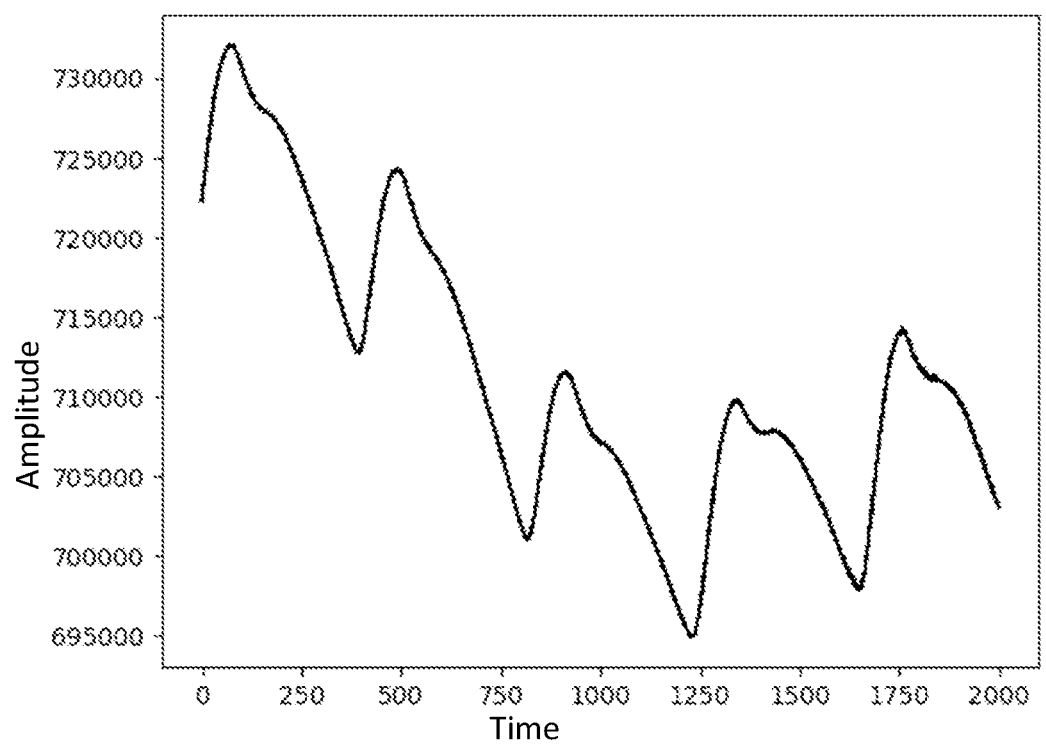
FIG. 11 is an example of raw PPG data.
Figure 12:
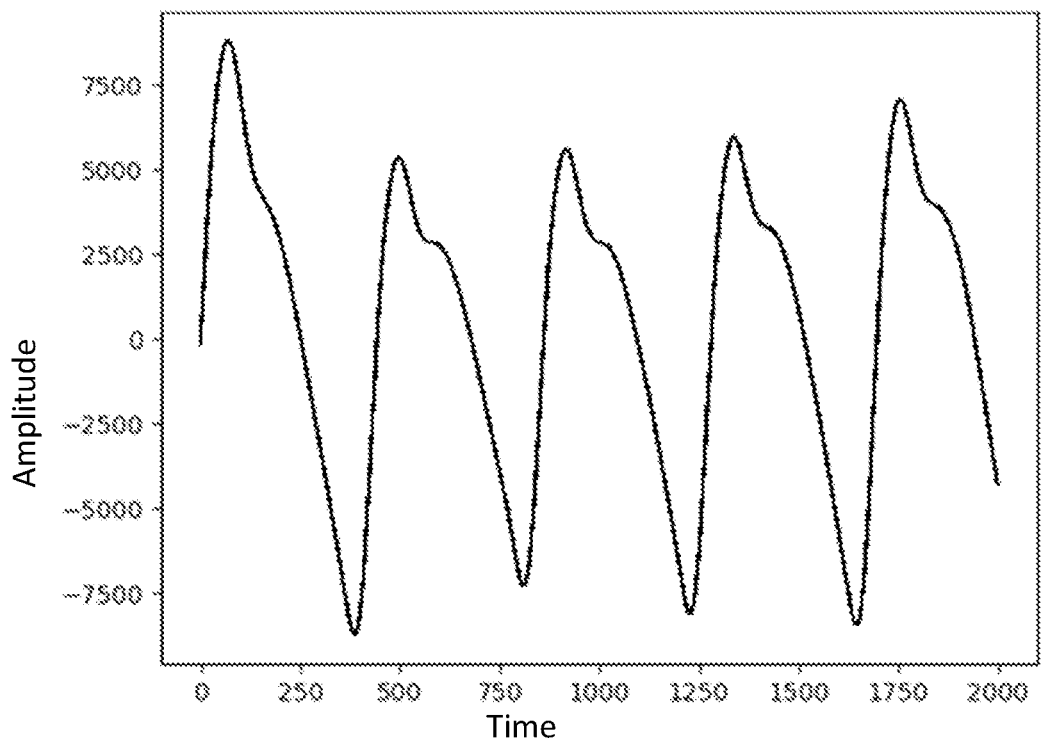
FIG. 12 is an example of filtered PPG data.

A further example of steps that may be carried out by an algorithm in a further embodiment of the invention will now be described with reference to FIGS. 11 to 20. Here, FIG. 11 is a graph of an example of raw PPG data in which several cardiac cycles can be seen clearly, these cycles being more or less suppressed by a respiratory cycle (hence the amplitude variations in the peaks). Such respiratory-induced amplitude variation is well known in the art and is caused by changes in pressure within the subject's chest caused by the subject's breathing. FIG. 12 is a graph of the same data as that shown in FIG. 11, with the low frequency (respiratory) signal filtered out. A 0.5-4 Hz filter is used to achieve this.

Figure 13:
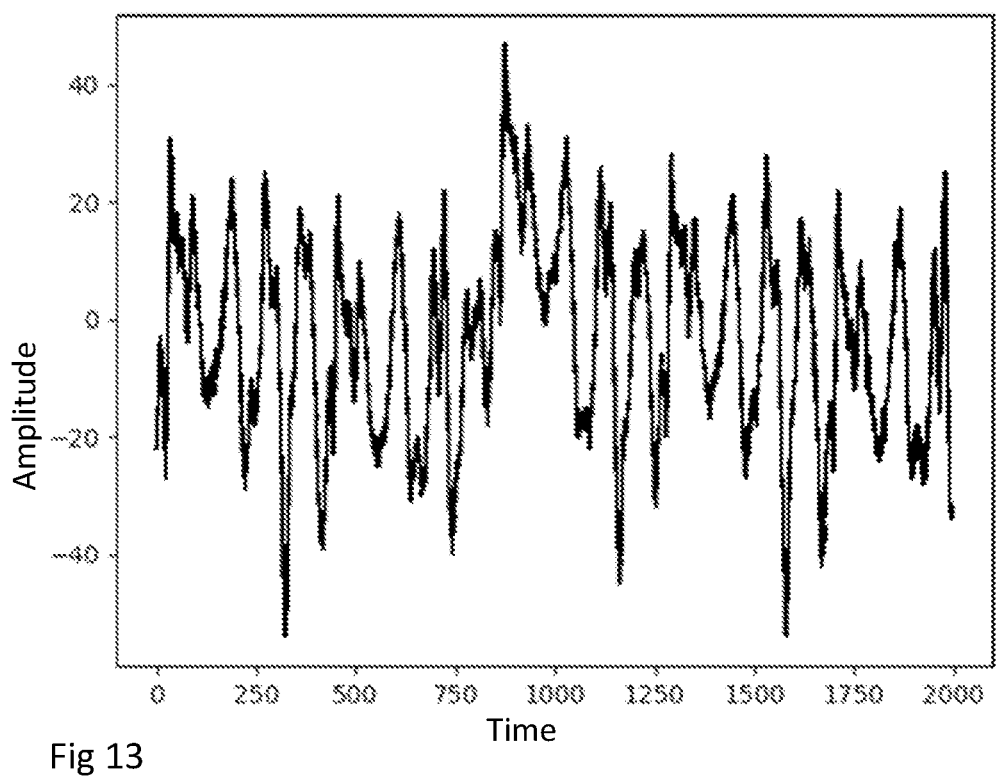
FIG. 13 is an example of raw single axis gyroscope data.

The data of the graph in FIG. 13 is an example of raw data as recorded by a single axis gyroscope. It may be seen that the data contains cycles; however, it also contains some higher frequency noise signals. In the graph in FIG. 14 the data of the graph in FIG. 13 has been filtered to remove these higher frequency noise signals (using a 4-12 Hz filter), resulting in a smoother sinusoidal waveform.

Figure 14:
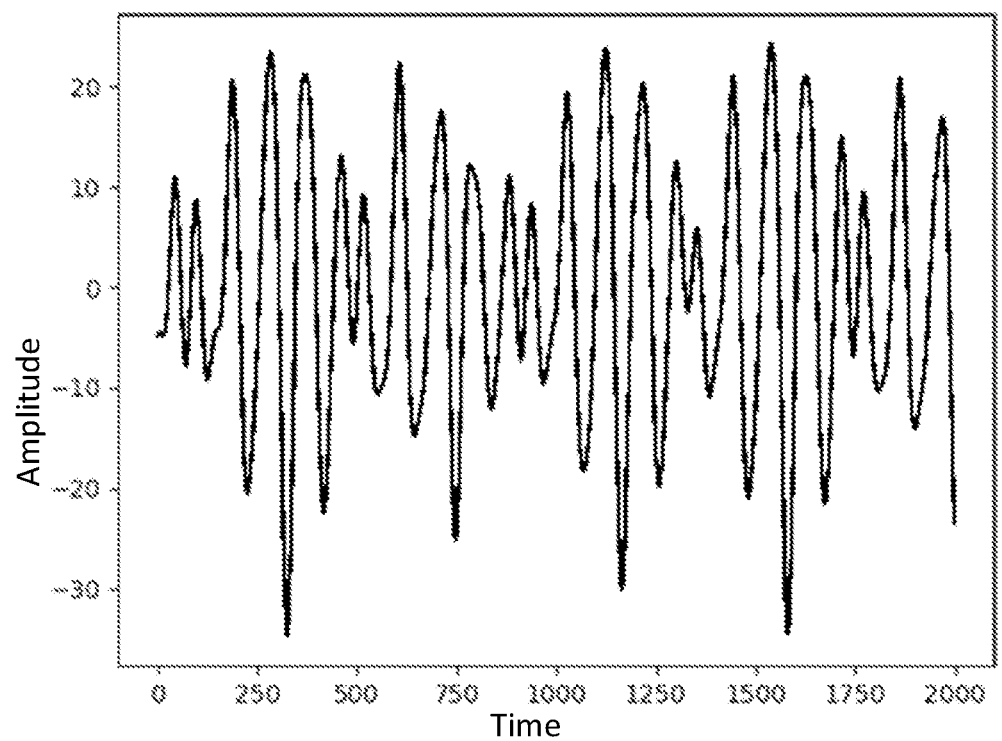
FIG. 14 is an example of filtered single axis gyroscope date.
Figure 15:
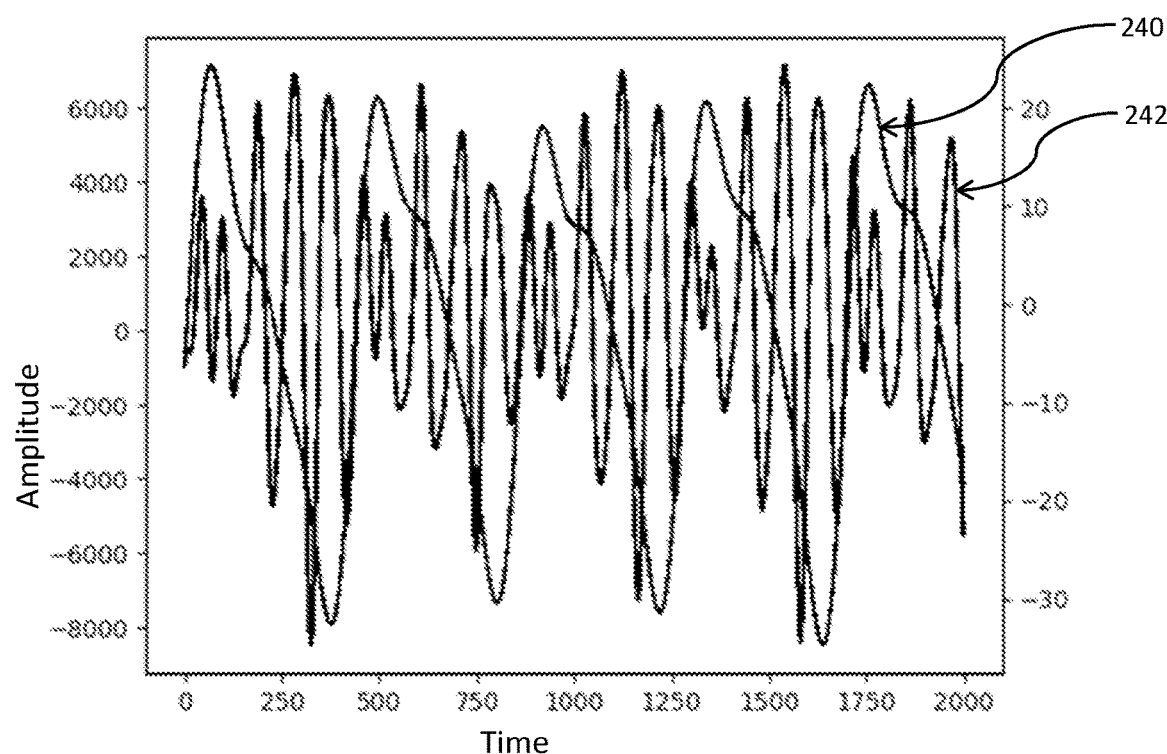
FIG. 15 is an example of filtered PPG data overlaid with filtered single axis gyroscope data.
Figure 16:
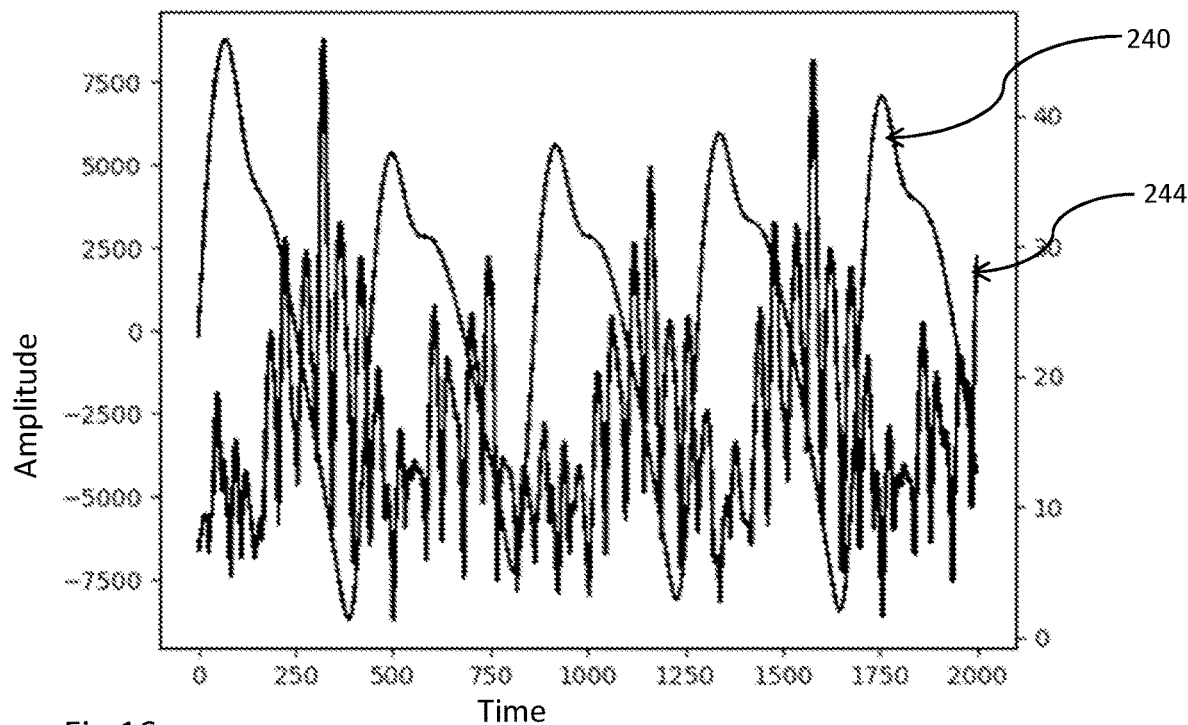
FIG. 16 is an example of absolute single axis gyroscope data overlaid with filtered PPG data.
Figure 17:
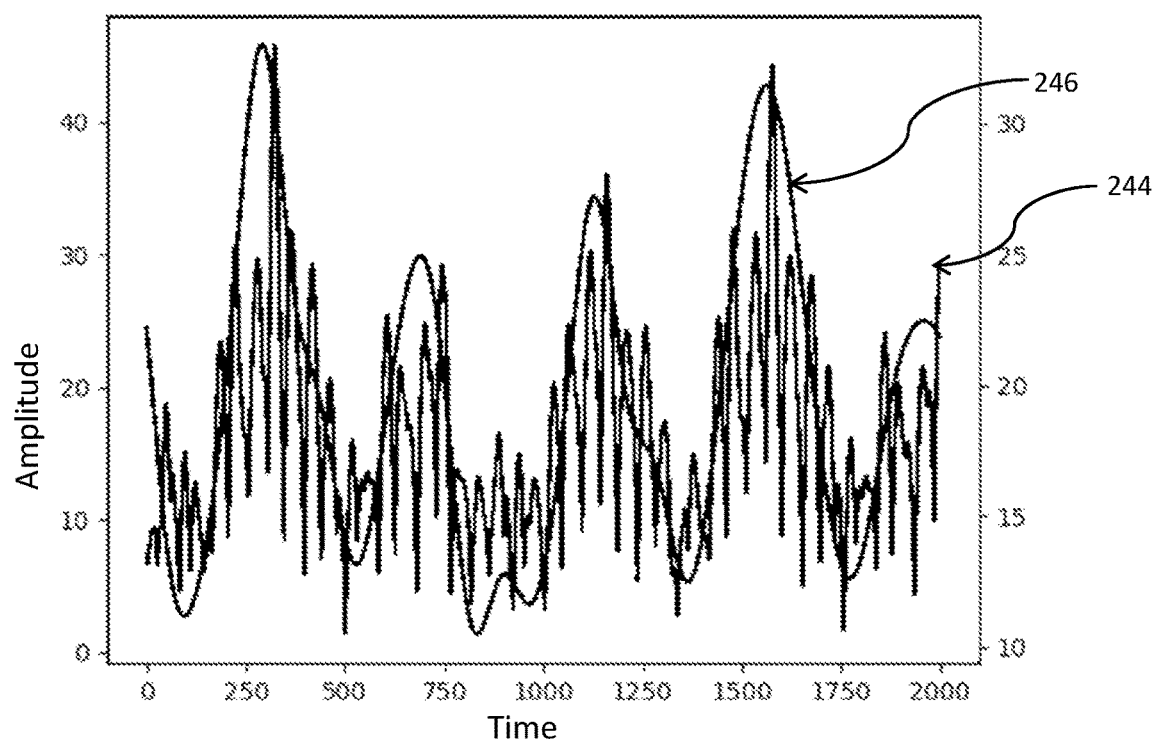
FIG. 17 is an example of single axis gyroscope data and a cubic spline interpolation of the single axis gyroscope data.

FIG. 15 is a graph the data of FIG. 12 (240) and the data of FIG. 14 (242). In the graph shown in FIG. 16, the absolute values of the single axis gyroscope data (244) have been calculated, such that the resulting waveform (244) never crosses the y-axis (i.e. the waveform never has a negative value). FIG. 17 provides the results of the next step of this embodiment, wherein a cubic spline interpolation (246) has been carried out on the gyroscope data. Here it is easier to compare the two signals by eye (however this step and any by-eye comparison are not necessary and in some example embodiments of the invention this step would be omitted).

It should be understood that the BCG signal can be found in the outputs of the gyroscopes and/or of the accelerometers. Therefore, there are several options for extracting the BCG signals from either the gyroscope output data, or the accelerometer output data, or both. For example, it may be that, first each axis of gyroscope output data may be summed, and then an absolute value of the summed gyroscope output data may be calculated, or these two steps might be carried out in the opposite order. Alternatively or additionally, first each axis of accelerometer data may be summed, and then an absolute value of the summed accelerometer output data may be calculated (again, these steps may be carried out in the opposite order). Or, in some examples, data associated with each axis may be considered individually. Where both gyroscope and accelerometer data are used the data must be normalised to take account of the different units of measurement.

Figure 18:
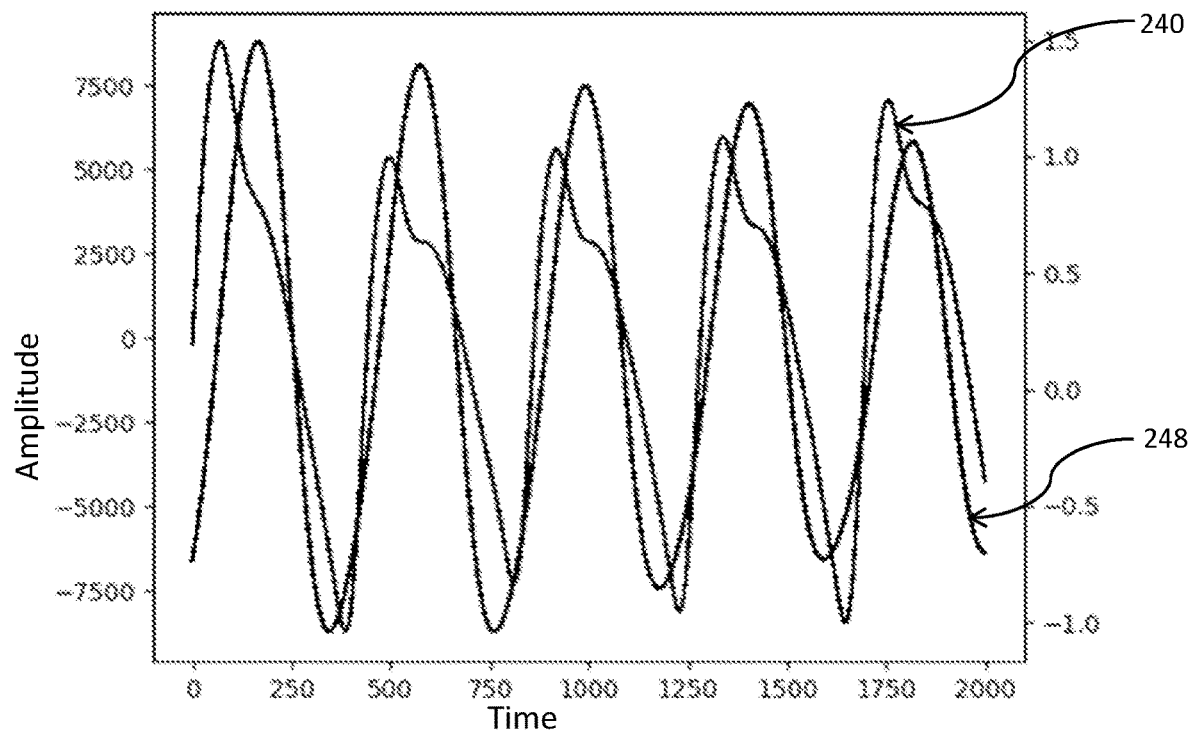
FIG. 18 is an example of a cross-correlation of absolute single axis gyroscope data overlaid with PPG data.
Figure 19:
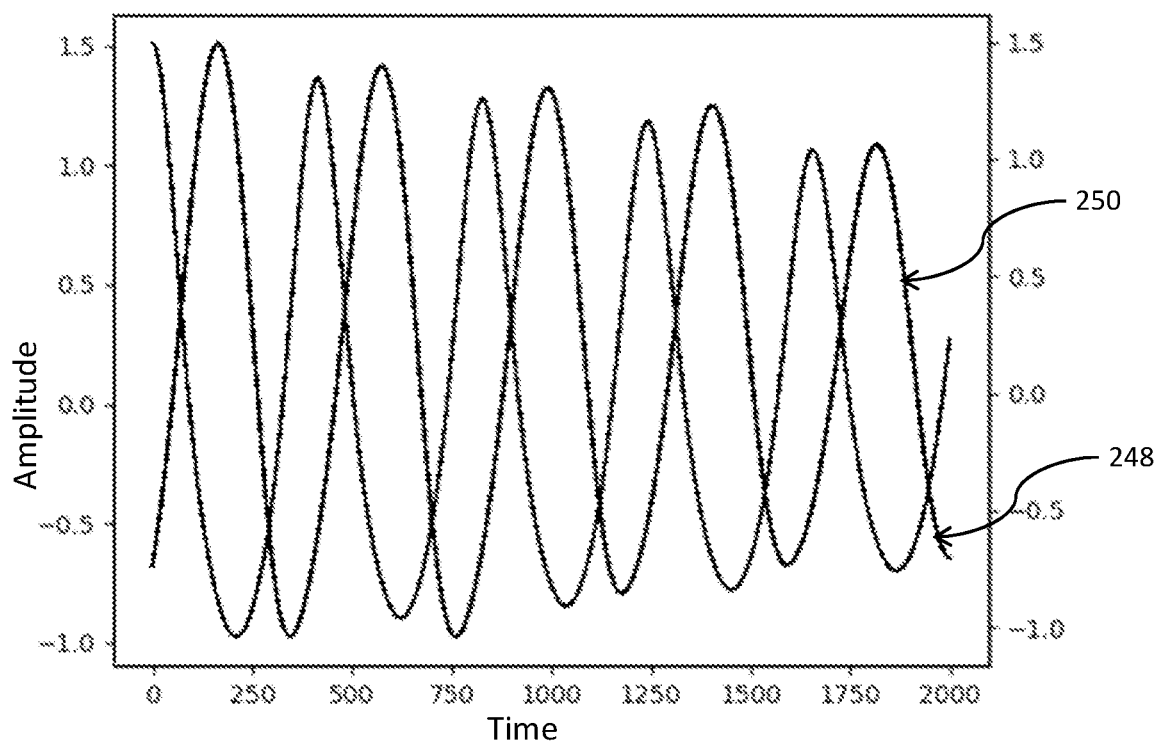
FIG. 19 is an example of a cross-correlation of absolute single axis gyroscope data overlaid with an example of an autocorrelation of PPG data.
Figure 20:
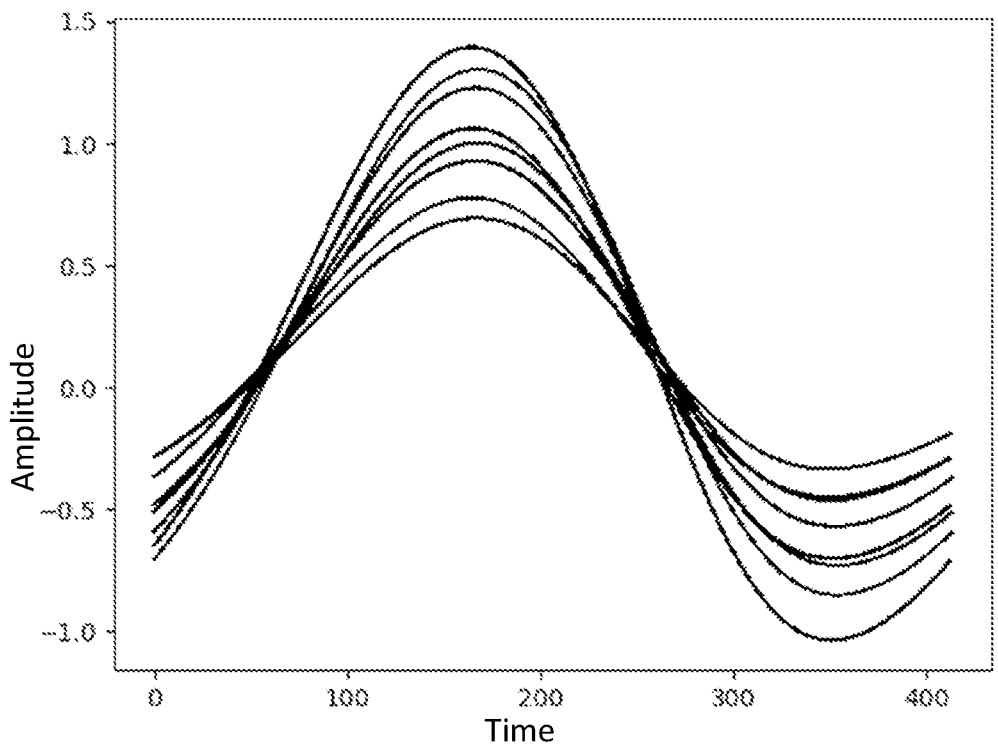
FIG. 20 is an example of several data windows.

In the graph of FIG. 18 a cross-correlation of the absolute single axis gyroscope data with the PPG data has been carried out, resulting in a cross-correlation waveform (248). Filtered PPG data (240) is also shown. In the graph of FIG. 19, the cross-correlation waveform (248) is shown and an autocorrelation of the PPG has been carried out (giving an autocorrelation waveform (250)) with the result that the two signals now have the same frequency and can be compared directly. This step is helpful as it is not necessarily immediately clear which part of the cardiac cycle will be taking place when the measurement is initiated. By autocorrelating the PPG signal, corresponding parts of each cardiac cycled are identified. The peaks of the autocorrelation waveform can then be used to guide where the data should be divided into individual windows of data, such that each window contains one cycle. FIG. 20 is a graph containing several such cycles overlaid on the same set of axes.

The instantaneous PTT (iPTT) can hence be calculated as the time between the largest peak in the cross-correlation waveform and the end of the window of data. The overall PTT can be calculated as an average (for example, a median) of the iPTTs. One skilled in the art will appreciate that more data will result in a greater number of windows and therefore a more reliable value of PTT, however, if the rate of change of PTT is required then data is measured over a longer period and PTT may be calculated once per hour, or twice per hour, for example.

The invention claimed is:

1. A monitoring apparatus for monitoring a pulse transit time (PTT) parameter of a subject, or changes therein, the monitoring apparatus comprising an upper arm unit, adapted to be worn on a subject's upper arm,
    the upper arm unit comprising at least one motion sensor, the at least one motion sensor configured to monitor motion due to cardiac activity and output at least one motion signal while the upper arm unit is adapted to be worn on the subject's upper arm,
    a photoplethysmograph (PPG) configured to monitor blood volume within the subject's upper arm and output a PPG signal while the upper arm unit is adapted to be worn on the subject's upper arm,
    at least one processor programmed to process both the at least one motion signal and the PPG signal to thereby calculate an estimate of the PTT parameter of the subject, or changes therein,
    wherein the processing both the at least one motion signal and the PPG signal comprises cross-calculating the at least one motion signal with the PPG signal, wherein cross-calculating the at least one motion signal with the PPG signal comprises time shifting the PPG signal and calculating an integral of a product of the at least one motion signal and the time-shifted PPG signal, across time shifts.

2. A monitoring apparatus according to claim 1 wherein the at least one motion sensor is a gyroscope and/or an accelerometer.

3. A monitoring apparatus according to claim 1 wherein the at least one processor comprises a clock, the clock configured to provide a shared clock signal for sampling of both the at least one motion signal and the PPG signal.

4. A monitoring apparatus according to claim 1, wherein the PPG comprises at least one light source, the at least one light source comprising at least one LED and at least one light detector, the at least one light detector comprising at least one photodiode.

5. A monitoring apparatus according to claim 1, wherein the monitoring apparatus further comprises a wireless transmitter configured to transmit data to at least one further device.

6. A method of monitoring a pulse transit time (PTT) parameter of a subject, or changes therein using a monitoring apparatus, the monitoring apparatus comprising an upper arm unit adapted to be worn on a subject's upper arm,
    the upper arm unit comprising at least one motion sensor, the at least one motion sensor configured to monitor motion due to cardiac activity and output at least one motion signal while the upper arm unit is worn on the subject's upper arm,
    a photoplethysmograph (PPG) configured to monitor blood volume within the subject's upper arm and output a PPG signal while the upper arm unit is worn on the subject's upper arm,
    the method comprising processing both the at least one motion signal and the PPG signal to thereby calculate an estimate of the PTT parameter of the subject, or changes therein and then outputting the calculated estimate of the PTT parameter of the subject, or changes therein,
    wherein the processing both the at least one motion signal and the PPG signal comprises cross-calculating the at least one motion signal with the PPG signal, wherein cross-calculating the at least one motion signal with the PPG signal comprises time shifting the PPG signal and calculating an integral of a product of the at least one motion signal and the time-shifted PPG signal, across time shifts.

7. A method according to claim 6, the method comprising processing the estimate of the PTT parameter of the subject to thereby calculate an estimate of one or more blood pressure (BP) parameters of the subject and then outputting the calculated estimate of the one or more BP parameters of the subject.

8. A method according to claim 6 wherein the method further comprises processing both the at least one motion signal and the PPG signal to thereby calculate an estimate of a rate of change of the PTT parameter of the subject, and then outputting the calculated estimate of the rate of change of the PTT parameter of the subject.

9. A method according to claim 6 wherein the method further comprises processing both the at least one motion signal and the PPG signal to thereby calculate an estimate of a rate of change of the PTT parameter of the subject, and further processing the estimate of the rate of change of the PTT parameter of the subject to calculate an estimate of a rate of change of one or more BP parameters of the subject, and then outputting the calculated estimate of the rate of change of the one or more BP parameters of the subject.

10. A method according to claim 6 wherein the processing comprises comparing a phase of at least one waveform derived from the at least one motion signal with a phase of at least one waveform derived from the PPG signal.

11. A method according to claim 6 wherein the processing comprises using the PPG signal as a baseline signal and comparing the at least one motion signal with this baseline signal throughout cardiac cycles to thereby calculate an estimate of the PTT parameter.

12. A method according to claim 6 wherein the processing comprises extracting a waveform representative of a cardiac cycle from the at least one motion signal by using the PPG signal as a reference and determining a timing difference between corresponding arbitrary points of the extracted waveform and a PPG derived waveform.

13. A method according to claim 6 wherein the processing comprises calculating a difference in time between a first instant when a first feature appears in at least one waveform derived from the at least one motion signal and a second instant when a corresponding feature appears in at least one waveform derived from the PPG signal.

14. A method according to claim 6 wherein the cross-calculating comprises cross-correlating the at least one motion signal with the PPG signal, and the processing further comprises auto-correlating the PPG signal.

15. A method according to claim 6 wherein the processing comprises analysing whether the output from the at least one motion sensor meets one or more quality criteria.

\* \* \* \* \*